(12) United States Patent
Siegel et al.

(10) Patent No.: US 12,702,549 B2
(45) Date of Patent: Aug. 11, 2026

(54) PROSTHETIC HEART VALVE

(71) Applicant: EDWARDS LIFESCIENCES CORPORATION, Irvine, CA (US)

(72) Inventors: Alexander J. Siegel, Irvine, CA (US); George Bakis, La Habra Heights, CA (US); Lien-Huong T. Hoang, San Juan Capistrano, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 18/324,906

(22) Filed: May 26, 2023

(65) Prior Publication Data

US 2023/0301782 A1 Sep. 28, 2023

Related U.S. Application Data

(60) Continuation of application No. 16/902,373, filed on Jun. 16, 2020, now abandoned, which is a (Continued)

(51) Int. Cl.
*A61F 2/24* (2006.01)
*A61M 25/00* (2006.01)
(Continued)

(52) U.S. Cl.
CPC .............. *A61F 2/2418* (2013.01); *A61F 2/24* (2013.01); *A61F 2/2415* (2013.01); (Continued)

(58) Field of Classification Search
CPC ......................................................... A61F 2/24
See application file for complete search history.

(56) References Cited

U.S. PATENT DOCUMENTS 30,912 A 12/1860 Hancock
2,343,225 A 2/1944 Holden et al.
(Continued)

FOREIGN PATENT DOCUMENTS

AU 2002212418 B2 3/2006
AU 2013200536 A1 2/2013
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Jacqueline Woznicki
(74) *Attorney, Agent, or Firm* — Klarquist Sparkman LLP

(57) ABSTRACT

The present disclosure is directed to embodiments of catheter-based prosthetic heart valves. In one embodiment, a prosthetic heart valve includes a collapsible and expandable annular frame, a leaflet assembly mounted within the annular frame, a first skirt mounted on the frame, and a second skirt mounted on the frame. The frame includes a plurality of rows of cells. The leaflet assembly includes a plurality of leaflets. Adjacent leaflets are connected to each other to form commissures, each of which is connected to a cell of an outflow row of cells of the frame. Inflow end portions of the leaflets are sutured to an outflow end portion of the first skirt along undulating suture line.

21 Claims, 23 Drawing Sheets

Related U.S. Application Data continuation of application No. 16/827,612, filed on Mar. 23, 2020, now abandoned, which is a continuation of application No. 16/150,035, filed on Oct. 2, 2018, now Pat. No. 10,595,993, which is a division of application No. 14/561,102, filed on Dec. 4, 2014, now Pat. No. 10,098,734.

(60) Provisional application No. 61/912,231, filed on Dec. 5, 2013.

(51) Int. Cl.

| | |
|---|---|
| ***A61M 25/01*** | (2006.01) |
| ***A61M 25/06*** | (2006.01) |
| ***B29C 49/24*** | (2006.01) |
| ***B29C 49/26*** | (2006.01) |
| *B29C 63/34* | (2006.01) |
| *B29K 101/12* | (2006.01) |
| *B29K 705/00* | (2006.01) |

(52) U.S. Cl.

CPC ....... *A61F 2/2436* (2013.01); *A61M 25/0045* (2013.01); *A61M 25/0051* (2013.01); *A61M 25/01* (2013.01); *A61M 25/0662* (2013.01); *B29C 49/24* (2013.01); *B29C 49/26* (2013.01); *A61F 2/2439* (2013.01); *A61F 2/2475* (2013.01); *A61F 2210/0076* (2013.01); *A61F 2220/0075* (2013.01); *A61F 2240/001* (2013.01); *A61F 2250/0039* (2013.01); *A61F 2250/006* (2013.01); *A61F 2250/0069* (2013.01); *A61M 25/0023* (2013.01); *B29C 2049/2404* (2013.01); *B29C 63/34* (2013.01); *B29K 2101/12* (2013.01); *B29K 2705/00* (2013.01)

(56) References Cited

U.S. PATENT DOCUMENTS

| | | | |
|---|---|---|---|
| 2,417,881 | A | 3/1947 | Munger |
| 2,440,725 | A | 5/1948 | Munger |
| 2,724,672 | A | 11/1955 | Rubin |
| 3,365,728 | A | 1/1968 | Lowell et al. |
| 3,409,013 | A | 11/1968 | Berry |
| 3,472,230 | A | 10/1969 | Fogarty |
| 3,548,417 | A | 12/1970 | Kisher |
| 3,587,115 | A | 6/1971 | Shiley |
| 3,657,744 | A | 4/1972 | Ersek |
| 3,671,979 | A | 6/1972 | Moulopoulos |
| 3,714,671 | A | 2/1973 | Edwards et al. |
| 3,725,961 | A | 4/1973 | Magovern et al. |
| 3,755,823 | A | 9/1973 | Hancock |
| 3,983,581 | A | 10/1976 | Angell et al. |
| 4,035,849 | A | 7/1977 | Angell et al. |
| 4,056,854 | A | 11/1977 | Boretos et al. |
| 4,106,129 | A | 8/1978 | Carpentier et al. |
| 4,222,126 | A | 9/1980 | Boretos et al. |
| 4,265,694 | A | 5/1981 | Boretos et al. |
| 4,297,749 | A | 11/1981 | Davis et al. |
| RE30,912 | E | 4/1982 | Hancock |
| 4,339,831 | A | 7/1982 | Johnson |
| 4,343,048 | A | 8/1982 | Ross et al. |
| 4,345,340 | A | 8/1982 | Rosen |
| 4,373,216 | A | 2/1983 | Klawitter |
| 4,406,022 | A | 9/1983 | Roy |
| 4,441,216 | A | 4/1984 | Ionescu et al. |
| 4,470,157 | A | 9/1984 | Love |
| 4,491,986 | A | 1/1985 | Gabbay |
| 4,501,030 | A | 2/1985 | Lane |
| 4,535,483 | A | 8/1985 | Klawitter et al. |
| 4,574,803 | A | 3/1986 | Storz |
| 4,592,340 | A | 6/1986 | Boyles |
| 4,605,407 | A | 8/1986 | Black et al. |
| 4,612,011 | A | 9/1986 | Kautzky |
| 4,629,459 | A | 12/1986 | Ionescu et al. |
| 4,643,732 | A | 2/1987 | Pietsch et al. |
| 4,655,771 | A | 4/1987 | Wallsten |
| 4,692,164 | A | 9/1987 | Dzemeshkevich et al. |
| 4,705,511 | A | 11/1987 | Kocak |
| 4,733,665 | A | 3/1988 | Palmaz |
| 4,759,758 | A | 7/1988 | Gabbay |
| 4,762,128 | A | 8/1988 | Rosenbluth |
| 4,777,951 | A | 10/1988 | Cribier et al. |
| 4,787,899 | A | 11/1988 | Lazarus |
| 4,787,901 | A | 11/1988 | Baykut |
| 4,796,629 | A | 1/1989 | Grayzel |
| 4,820,299 | A | 4/1989 | Philippe et al. |
| 4,829,990 | A | 5/1989 | Thuroff et al. |
| 4,851,001 | A | 7/1989 | Taheri |
| 4,856,516 | A | 8/1989 | Hillstead |
| 4,878,495 | A | 11/1989 | Grayzel |
| 4,878,906 | A | 11/1989 | Lindemann et al. |
| 4,883,458 | A | 11/1989 | Shiber |
| 4,922,905 | A | 5/1990 | Strecker |
| 4,966,604 | A | 10/1990 | Reiss |
| 4,979,939 | A | 12/1990 | Shiber |
| 4,986,830 | A | 1/1991 | Owens et al. |
| 4,994,077 | A | 2/1991 | Dobben |
| 5,007,896 | A | 4/1991 | Shiber |
| 5,026,366 | A | 6/1991 | Leckrone |
| 5,032,128 | A | 7/1991 | Alonso |
| 5,037,434 | A | 8/1991 | Lane |
| 5,047,041 | A | 9/1991 | Samuels |
| 5,059,177 | A | 10/1991 | Towne et al. |
| 5,080,668 | A | 1/1992 | Bolz et al. |
| 5,085,635 | A | 2/1992 | Cragg |
| 5,089,015 | A | 2/1992 | Ross |
| 5,108,370 | A | 4/1992 | Walinsky |
| 5,141,494 | A | 8/1992 | Danforth et al. |
| 5,152,771 | A | 10/1992 | Sabbaghian et al. |
| 5,163,953 | A | 11/1992 | Vince |
| 5,167,628 | A | 12/1992 | Boyles |
| 5,180,376 | A | 1/1993 | Fischell |
| 5,192,297 | A | 3/1993 | Hull |
| 5,222,949 | A | 6/1993 | Kaldany |
| 5,232,446 | A | 8/1993 | Arney |
| 5,258,023 | A | 11/1993 | Reger |
| 5,266,073 | A | 11/1993 | Wall |
| 5,282,847 | A | 2/1994 | Trescony et al. |
| 5,295,958 | A | 3/1994 | Shturman |
| 5,300,032 | A | 4/1994 | Hibbs et al. |
| 5,332,402 | A | 7/1994 | Teitelbaum |
| 5,360,444 | A | 11/1994 | Kusuhara |
| 5,370,685 | A | 12/1994 | Stevens |
| 5,397,351 | A | 3/1995 | Pavcnik et al. |
| 5,411,055 | A | 5/1995 | Kane |
| 5,411,522 | A | 5/1995 | Trott |
| 5,411,552 | A | 5/1995 | Andersen et al. |
| 5,443,446 | A | 8/1995 | Shturman |
| 5,476,506 | A | 12/1995 | Lunn |
| 5,480,424 | A | 1/1996 | Cox |
| 5,500,014 | A | 3/1996 | Quijano et al. |
| 5,545,209 | A | 8/1996 | Roberts et al. |
| 5,545,214 | A | 8/1996 | Stevens |
| 5,549,665 | A | 8/1996 | Vesely et al. |
| 5,554,185 | A | 9/1996 | Block et al. |
| 5,558,644 | A | 9/1996 | Boyd et al. |
| 5,571,175 | A | 11/1996 | Vanney et al. |
| 5,584,803 | A | 12/1996 | Stevens et al. |
| 5,591,185 | A | 1/1997 | Kilmer et al. |
| 5,591,195 | A | 1/1997 | Taheri et al. |
| 5,599,305 | A | 2/1997 | Hermann et al. |
| 5,607,464 | A | 3/1997 | Trescony et al. |
| 5,609,626 | A | 3/1997 | Quijano et al. |
| 5,628,786 | A | 5/1997 | Banas et al. |
| 5,628,792 | A | 5/1997 | Lentell |
| 5,639,274 | A | 6/1997 | Fischell et al. |
| 5,665,115 | A | 9/1997 | Cragg |
| 5,693,088 | A | 12/1997 | Lazarus |
| 5,716,417 | A | 2/1998 | Girard et al. |
| 5,728,068 | A | 3/1998 | Leone et al. |
| 5,749,890 | A | 5/1998 | Shaknovich |

(56) References Cited

U.S. PATENT DOCUMENTS 5,755,783 A 5/1998 Stobie et al.
5,756,476 A 5/1998 Epstein et al.
5,769,812 A 6/1998 Stevens et al.
5,769,882 A 6/1998 Fogarty et al.
5,776,188 A 7/1998 Shepherd et al.
5,800,508 A 9/1998 Goicoechea et al.
5,840,081 A 11/1998 Andersen et al.
5,843,161 A 12/1998 Solovay
5,843,179 A 12/1998 Vanney et al.
5,855,597 A 1/1999 Jayaraman
5,855,601 A 1/1999 Bessler et al.
5,855,602 A 1/1999 Angell
5,925,063 A 7/1999 Khosravi
5,957,949 A 9/1999 Leonhardt et al.
5,968,068 A 10/1999 Dehdashtian et al.
5,980,570 A 11/1999 Simpson
5,984,959 A 11/1999 Robertson et al.
6,015,431 A 1/2000 Thornton et al.
6,027,525 A 2/2000 Suh et al.
6,042,607 A 3/2000 Williamson, IV et al.
6,110,198 A 8/2000 Fogarty et al.
6,132,473 A 10/2000 Williams et al.
6,168,614 B1 1/2001 Andersen et al.
6,171,335 B1 1/2001 Wheatley et al.
6,174,327 B1 1/2001 Mertens et al.
6,206,911 B1 3/2001 Milo
6,210,408 B1 4/2001 Chandrasekaran et al.
6,217,585 B1 4/2001 Houser et al.
6,221,091 B1 4/2001 Khosravi
6,231,602 B1 5/2001 Carpentier et al.
6,245,040 B1 6/2001 Inderbitzen et al.
6,245,102 B1 6/2001 Jayaraman
6,299,637 B1 10/2001 Shaolian et al.
6,302,906 B1 10/2001 Goicoechea et al.
6,306,164 B1 10/2001 Kujawski et al.
6,338,740 B1 1/2002 Carpentier
6,350,277 B1 2/2002 Kocur
6,352,547 B1 3/2002 Brown et al.
6,352,554 B2 3/2002 De
6,398,814 B1 6/2002 Paasimaa et al.
6,419,695 B1 7/2002 Gabbay
6,425,916 B1 7/2002 Garrison et al.
6,440,764 B1 8/2002 Focht et al.
6,454,799 B1 9/2002 Schreck
6,458,153 B1 10/2002 Bailey et al.
6,461,382 B1 10/2002 Cao
6,468,660 B2 10/2002 Ogle et al.
6,482,228 B1 11/2002 Norred
6,488,704 B1 12/2002 Connelly et al.
6,527,979 B2 3/2003 Constantz et al.
6,540,782 B1 4/2003 Snyders
6,569,196 B1 5/2003 Vesely
6,575,959 B1 6/2003 Sarge et al.
6,582,462 B1 6/2003 Andersen et al.
6,605,112 B1 8/2003 Moll et al.
6,652,578 B2 11/2003 Bailey et al.
6,663,667 B2 12/2003 Dehdashtian et al.
6,689,123 B2 2/2004 Pinchasik
6,716,244 B2 4/2004 Klaco
6,729,356 B1 5/2004 Baker et al.
6,730,118 B2 5/2004 Spenser et al.
6,733,525 B2 5/2004 Yang et al.
6,767,362 B2 7/2004 Schreck
6,769,161 B2 8/2004 Brown et al.
6,773,456 B1 8/2004 Gordon et al.
6,783,542 B2 8/2004 Eidenschink
6,814,754 B2 11/2004 Greenhalgh
6,830,584 B1 12/2004 Seguin
6,869,444 B2 3/2005 Gabbay
6,878,162 B2 4/2005 Bales et al.
6,893,460 B2 5/2005 Spenser et al.
6,904,909 B2 6/2005 Andreas et al.
6,908,481 B2 6/2005 Cribier
6,911,040 B2 6/2005 Johnson et al.
6,936,067 B2 8/2005 Buchanan
7,018,406 B2 3/2006 Seguin et al.
7,018,408 B2 3/2006 Bailey et al.
7,096,554 B2 8/2006 Austin et al.
7,147,663 B1 12/2006 Berg et al.
7,160,322 B2 1/2007 Gabbay
7,225,518 B2 6/2007 Eidenschink et al.
7,264,632 B2 9/2007 Wright et al.
7,276,078 B2 10/2007 Spenser et al.
7,276,084 B2 10/2007 Yang et al.
7,316,710 B1 1/2008 Cheng et al.
7,318,278 B2 1/2008 Zhang et al.
7,374,571 B2 5/2008 Pease et al.
7,381,210 B2 6/2008 Zarbatany et al.
7,393,360 B2 7/2008 Spenser et al.
7,462,191 B2 12/2008 Spenser et al.
7,510,575 B2 3/2009 Spenser et al.
7,563,280 B2 7/2009 Anderson et al.
7,579,381 B2 8/2009 Dove
7,585,321 B2 9/2009 Cribier
7,618,446 B2 11/2009 Andersen et al.
7,618,447 B2 11/2009 Case et al.
7,621,948 B2 11/2009 Herrmann et al.
7,655,034 B2 2/2010 Mitchell et al.
7,682,381 B2 3/2010 Rakos et al.
7,731,742 B2 6/2010 Schlick et al.
7,780,725 B2 8/2010 Haug et al.
7,785,366 B2 8/2010 Maurer et al.
7,959,665 B2 6/2011 Pienknagura
7,959,672 B2 6/2011 Salahieh et al.
7,993,394 B2 8/2011 Hariton et al.
8,007,992 B2 8/2011 Tian et al.
8,029,556 B2 10/2011 Rowe
8,075,611 B2 12/2011 Millwee et al.
8,105,375 B2 1/2012 Navia et al.
8,128,681 B2 3/2012 Shoemaker et al.
8,128,686 B2 3/2012 Paul, Jr. et al.
8,167,932 B2 5/2012 Bourang et al.
8,291,570 B2 10/2012 Eidenschink et al.
8,343,136 B2 1/2013 Howat et al.
8,348,963 B2 1/2013 Wilson
8,348,998 B2 1/2013 Pintor et al.
8,403,896 B2 3/2013 Leeflang et al.
8,449,606 B2 5/2013 Eliasen et al.
8,454,685 B2 6/2013 Hariton et al.
8,652,203 B2 2/2014 Quadri et al.
8,685,055 B2 4/2014 Vantassel et al.
8,721,717 B2 5/2014 Shoemaker et al.
8,747,463 B2 6/2014 Fogarty et al.
8,795,357 B2 8/2014 Yohanan et al.
8,968,419 B2 3/2015 Calvez et al.
9,078,781 B2 7/2015 Ryan et al.
9,597,430 B2 3/2017 Ratcliffe et al.
9,655,389 B2 5/2017 Blakely
9,668,856 B2 6/2017 Para
9,820,852 B2 11/2017 Braido et al.
11,224,509 B2 1/2022 Dasi et al.
2001/0021872 A1 9/2001 Bailey et al.
2001/0027338 A1 10/2001 Greenberg
2001/0039450 A1 11/2001 Pavcnik et al.
2002/0026094 A1 2/2002 Roth
2002/0032481 A1 3/2002 Gabbay
2002/0116070 A1 8/2002 Amara et al.
2002/0138135 A1 9/2002 Duerig et al.
2002/0143390 A1 10/2002 Ishii
2002/0173842 A1 11/2002 Buchanan
2003/0014105 A1 1/2003 Cao
2003/0040791 A1 2/2003 Oktay
2003/0050694 A1 3/2003 Yang et al.
2003/0069522 A1 4/2003 Jacobsen et al.
2003/0074058 A1 4/2003 Sherry
2003/0074628 A1 4/2003 Lee
2003/0100939 A1 5/2003 Yodfat et al.
2003/0158597 A1 8/2003 Quiachon et al.
2003/0212454 A1 11/2003 Scott et al.
2003/0236567 A1 12/2003 Elliot
2004/0024452 A1 2/2004 Kruse et al.
2004/0033364 A1 2/2004 Spiridigliozzi et al.
2004/0039436 A1 2/2004 Spenser et al.
2004/0078074 A1 4/2004 Anderson et al.

(56) References Cited

U.S. PATENT DOCUMENTS

| | | | |
|---|---|---|---|
| 2004/0082989 | A1 | 4/2004 | Cook et al. |
| 2004/0098096 | A1 | 5/2004 | Eton |
| 2004/0133263 | A1 | 7/2004 | Dusbabek et al. |
| 2004/0186558 | A1 | 9/2004 | Pavcnik et al. |
| 2004/0186563 | A1 | 9/2004 | Lobbi |
| 2004/0186565 | A1 | 9/2004 | Schreck |
| 2004/0210304 | A1 | 10/2004 | Seguin et al. |
| 2004/0219854 | A1 | 11/2004 | Groitzsch et al. |
| 2004/0260389 | A1 | 12/2004 | Case et al. |
| 2005/0010285 | A1 | 1/2005 | Lambrecht et al. |
| 2005/0043790 | A1 | 2/2005 | Seguin |
| 2005/0045566 | A1 | 3/2005 | Larkin et al. |
| 2005/0070930 | A1 | 3/2005 | Kammerer |
| 2005/0075724 | A1 | 4/2005 | Svanidze et al. |
| 2005/0075725 | A1 | 4/2005 | Rowe |
| 2005/0075728 | A1 | 4/2005 | Nguyen et al. |
| 2005/0096736 | A1 | 5/2005 | Osse et al. |
| 2005/0096738 | A1 | 5/2005 | Cali et al. |
| 2005/0137686 | A1 | 6/2005 | Salahieh et al. |
| 2005/0137687 | A1 | 6/2005 | Salahieh et al. |
| 2005/0149160 | A1 | 7/2005 | Mcferran |
| 2005/0188525 | A1 | 9/2005 | Weber et al. |
| 2005/0203614 | A1 | 9/2005 | Forster et al. |
| 2005/0203617 | A1 | 9/2005 | Forster et al. |
| 2005/0234546 | A1 | 10/2005 | Nugent et al. |
| 2005/0288766 | A1 | 12/2005 | Plain et al. |
| 2006/0004469 | A1 | 1/2006 | Sokel |
| 2006/0025857 | A1 | 2/2006 | Bergheim et al. |
| 2006/0058872 | A1 | 3/2006 | Salahieh et al. |
| 2006/0074484 | A1 | 4/2006 | Huber |
| 2006/0108090 | A1 | 5/2006 | Ederer et al. |
| 2006/0113906 | A1 | 6/2006 | Ogawa |
| 2006/0142837 | A1 | 6/2006 | Haverkost et al. |
| 2006/0149350 | A1 | 7/2006 | Patel et al. |
| 2006/0183383 | A1 | 8/2006 | Asmus et al. |
| 2006/0189896 | A1 | 8/2006 | Davis et al. |
| 2006/0229719 | A1 | 10/2006 | Marquez et al. |
| 2006/0259135 | A1 | 11/2006 | Navia et al. |
| 2006/0259136 | A1 | 11/2006 | Nguyen et al. |
| 2006/0259137 | A1 | 11/2006 | Artof et al. |
| 2006/0276886 | A1 | 12/2006 | George et al. |
| 2006/0287717 | A1 | 12/2006 | Rowe et al. |
| 2007/0005131 | A1 | 1/2007 | Taylor |
| 2007/0010876 | A1 | 1/2007 | Salahieh et al. |
| 2007/0010877 | A1 | 1/2007 | Salahieh et al. |
| 2007/0027534 | A1 | 2/2007 | Bergheim et al. |
| 2007/0073387 | A1 | 3/2007 | Forster et al. |
| 2007/0088431 | A1 | 4/2007 | Bourang et al. |
| 2007/0100285 | A1 | 5/2007 | Griffin et al. |
| 2007/0112422 | A1 | 5/2007 | Dehdashtian |
| 2007/0118210 | A1 | 5/2007 | Pinchuk |
| 2007/0156224 | A1 | 7/2007 | Cioanta et al. |
| 2007/0162102 | A1 | 7/2007 | Ryan et al. |
| 2007/0203503 | A1 | 8/2007 | Salahieh et al. |
| 2007/0203575 | A1 | 8/2007 | Forster et al. |
| 2007/0203576 | A1 | 8/2007 | Lee et al. |
| 2007/0208550 | A1 | 9/2007 | Cao et al. |
| 2007/0213813 | A1 | 9/2007 | Von Segesser et al. |
| 2007/0233228 | A1 | 10/2007 | Eberhardt et al. |
| 2007/0260305 | A1 | 11/2007 | Drews et al. |
| 2007/0265700 | A1 | 11/2007 | Eliasen et al. |
| 2007/0270943 | A1 | 11/2007 | Solem et al. |
| 2008/0021546 | A1 | 1/2008 | Patz et al. |
| 2008/0065011 | A1 | 3/2008 | Marchand et al. |
| 2008/0114442 | A1 | 5/2008 | Mitchell et al. |
| 2008/0125853 | A1 | 5/2008 | Bailey et al. |
| 2008/0147171 | A1 | 6/2008 | Ashton et al. |
| 2008/0154355 | A1 | 6/2008 | Benichou et al. |
| 2008/0161911 | A1 | 7/2008 | Revuelta et al. |
| 2008/0183271 | A1 | 7/2008 | Frawley et al. |
| 2008/0188928 | A1 | 8/2008 | Salahieh et al. |
| 2008/0200980 | A1 | 8/2008 | Robin et al. |
| 2008/0208327 | A1 | 8/2008 | Rowe |
| 2008/0243245 | A1 | 10/2008 | Thambar et al. |
| 2008/0255660 | A1 | 10/2008 | Guyenot et al. |
| 2008/0275537 | A1 | 11/2008 | Limon |
| 2008/0294230 | A1 | 11/2008 | Parker |
| 2008/0294248 | A1 | 11/2008 | Yang et al. |
| 2009/0088836 | A1 | 4/2009 | Bishop et al. |
| 2009/0099653 | A1 | 4/2009 | Suri et al. |
| 2009/0118826 | A1 | 5/2009 | Khaghani |
| 2009/0125118 | A1 | 5/2009 | Gong |
| 2009/0132035 | A1 | 5/2009 | Roth et al. |
| 2009/0157175 | A1 | 6/2009 | Benichou |
| 2009/0164005 | A1 | 6/2009 | Dove et al. |
| 2009/0171456 | A1 | 7/2009 | Kveen et al. |
| 2009/0221965 | A1 | 9/2009 | Osypka |
| 2009/0240320 | A1 | 9/2009 | Tuval et al. |
| 2009/0276040 | A1 | 11/2009 | Rowe et al. |
| 2009/0281619 | A1 | 11/2009 | Le et al. |
| 2009/0287296 | A1 | 11/2009 | Manasse |
| 2009/0287299 | A1 | 11/2009 | Tabor et al. |
| 2009/0299452 | A1 | 12/2009 | Eidenschink et al. |
| 2009/0319037 | A1 | 12/2009 | Rowe et al. |
| 2010/0004735 | A1 | 1/2010 | Yang et al. |
| 2010/0049313 | A1* | 2/2010 | Alon .................... A61F 2/2439 623/2.11 |
| 2010/0069852 | A1 | 3/2010 | Kelley |
| 2010/0082094 | A1 | 4/2010 | Quadri et al. |
| 2010/0100176 | A1 | 4/2010 | Elizondo et al. |
| 2010/0168844 | A1 | 7/2010 | Toomes et al. |
| 2010/0185277 | A1 | 7/2010 | Braido et al. |
| 2010/0198347 | A1 | 8/2010 | Zakay et al. |
| 2010/0204781 | A1 | 8/2010 | Alkhatib |
| 2010/0262233 | A1 | 10/2010 | He |
| 2010/0331972 | A1* | 12/2010 | Pintor .................. A61F 2/2418 623/2.11 |
| 2011/0004299 | A1 | 1/2011 | Essinger et al. |
| 2011/0015729 | A1 | 1/2011 | Jimenez et al. |
| 2011/0066224 | A1 | 3/2011 | White |
| 2011/0098802 | A1 | 4/2011 | Braido et al. |
| 2011/0137397 | A1 | 6/2011 | Chau et al. |
| 2011/0152763 | A1 | 6/2011 | Bishop et al. |
| 2011/0218619 | A1 | 9/2011 | Benichou et al. |
| 2011/0319991 | A1 | 12/2011 | Hariton et al. |
| 2012/0030090 | A1 | 2/2012 | Johnston et al. |
| 2012/0035719 | A1 | 2/2012 | Forster et al. |
| 2012/0065729 | A1 | 3/2012 | Pintor et al. |
| 2012/0078357 | A1 | 3/2012 | Conklin |
| 2012/0083877 | A1 | 4/2012 | Nguyen et al. |
| 2012/0089223 | A1 | 4/2012 | Nguyen et al. |
| 2012/0101571 | A1 | 4/2012 | Thambar et al. |
| 2012/0123529 | A1* | 5/2012 | Levi ...................... A61F 2/2418 623/2.11 |
| 2012/0215303 | A1 | 8/2012 | Quadri et al. |
| 2012/0259409 | A1 | 10/2012 | Nguyen et al. |
| 2012/0296418 | A1 | 11/2012 | Bonyuet et al. |
| 2013/0018458 | A1* | 1/2013 | Yohanan ............... A61F 2/2433 623/2.38 |
| 2013/0023985 | A1 | 1/2013 | Khairkhahan et al. |
| 2013/0046373 | A1 | 2/2013 | Cartledge et al. |
| 2013/0150956 | A1 | 6/2013 | Yohanan et al. |
| 2013/0166017 | A1 | 6/2013 | Cartledge et al. |
| 2013/0178795 | A1 | 7/2013 | Wilson et al. |
| 2013/0190857 | A1 | 7/2013 | Mitra et al. |
| 2013/0190862 | A1* | 7/2013 | Pintor .................. A61F 2/2403 623/2.18 |
| 2013/0197622 | A1 | 8/2013 | Mitra et al. |
| 2013/0253417 | A1 | 9/2013 | Dinh et al. |
| 2013/0260104 | A1 | 10/2013 | Dua et al. |
| 2013/0274873 | A1 | 10/2013 | Delaloye et al. |
| 2013/0310926 | A1 | 11/2013 | Hariton |
| 2013/0317598 | A1 | 11/2013 | Rowe et al. |
| 2013/0331929 | A1 | 12/2013 | Mitra et al. |
| 2014/0194981 | A1 | 7/2014 | Menk et al. |
| 2014/0200661 | A1 | 7/2014 | Pintor et al. |
| 2014/0209238 | A1 | 7/2014 | Bonyuet et al. |
| 2014/0214157 | A1 | 7/2014 | Bortlein |
| 2014/0222136 | A1 | 8/2014 | Geist et al. |
| 2014/0222142 | A1 | 8/2014 | Kovalsky et al. |
| 2014/0228945 | A1 | 8/2014 | Valdez et al. |
| 2014/0277417 | A1 | 9/2014 | Schraut et al. |
| 2014/0277419 | A1 | 9/2014 | Garde et al. |
| 2014/0277424 | A1 | 9/2014 | Oslund |

(56) References Cited

U.S. PATENT DOCUMENTS

2014/0277563 A1 9/2014 White
2014/0296962 A1 10/2014 Cartledge et al.
2014/0330372 A1 11/2014 Weston et al.
2014/0343670 A1 11/2014 Bakis et al.
2014/0343671 A1 11/2014 Yohanan et al.
2014/0350667 A1 11/2014 Braido et al.
2015/0039084 A1 2/2015 Levi et al.
2015/0073541 A1 3/2015 Salahieh et al.
2015/0073545 A1* 3/2015 Braido .................. A61F 2/2418 623/2.18
2015/0073546 A1 3/2015 Braido
2015/0135506 A1 5/2015 White
2015/0157455 A1 6/2015 Hoang et al.
2015/0173898 A1 6/2015 Drasler et al.
2015/0265402 A1 9/2015 Centola et al.
2015/0289973 A1 10/2015 Braido et al.
2015/0305860 A1 10/2015 Wang et al.
2016/0120646 A1 5/2016 Dwork et al.
2017/0014229 A1 1/2017 Nguyen-Thien-Nhon et al.
2017/0172736 A1 6/2017 Chadha et al.
2018/0028310 A1 2/2018 Gurovich et al.
2018/0110609 A1 4/2018 Ehnes et al.
2018/0153689 A1 6/2018 Maimon et al.
2018/0325665 A1 11/2018 Gurovich et al.
2018/0344456 A1 12/2018 Barash et al.

FOREIGN PATENT DOCUMENTS

CA 736910 A 6/1966
CN 1985775 A 6/2007
CN 101040797 A 9/2007
CN 101138877 A 3/2008
CN 101196264 A 6/2008
CN 101972177 A 2/2011
CN 202105047 U 1/2012
CN 103108611 A 5/2013
DE 0144167 C 9/1903
DE 2246526 A1 3/1973
DE 19532846 A1 3/1997
DE 19546692 A1 6/1997
DE 19857887 A1 7/2000
DE 19907646 A1 8/2000
DE 10049812 A1 4/2002
DE 10049813 C1 4/2002
DE 10049814 A1 4/2002
DE 10049815 A1 4/2002
EP 0103546 A1 3/1984
EP 0144167 A2 6/1985
EP 0850607 A1 7/1998
EP 1057460 A1 12/2000
EP 1088529 A2 4/2001
EP 1570809 A1 9/2005
EP 2745805 B1 6/2015
EP 2749254 B1 6/2015
FR 2788217 A1 7/2000
FR 2815844 A1 5/2002
GB 2056023 A 3/1981
GB 2222954 A 3/1990
JP S5453177 A 4/1979
SU 1271508 A1 11/1986
WO 9117720 A1 11/1991
WO 9217118 A1 10/1992
WO 9301768 A1 2/1993
WO 9724080 A1 7/1997
WO WO-1997048350 A1 12/1997
WO 9829057 A1 7/1998
WO 9930646 A1 6/1999
WO 9933414 A1 7/1999
WO 9940964 A1 8/1999
WO 9947075 A1 9/1999
WO 0018333 A1 4/2000
WO 0041652 A1 7/2000
WO 0047139 A1 8/2000
WO WO-2000044313 A1 8/2000
WO WO-2001006959 A1 2/2001
WO 0135878 A2 5/2001
WO 0149213 A2 7/2001
WO 0154624 A1 8/2001
WO 0154625 A1 8/2001
WO 0162189 A1 8/2001
WO 0164137 A1 9/2001
WO 0176510 A2 10/2001
WO 0222054 A1 3/2002
WO WO-2002019951 A1 3/2002
WO WO-2002028314 A2 4/2002
WO 0236048 A1 5/2002
WO 0241789 A2 5/2002
WO 0243620 A1 6/2002
WO 0247575 A2 6/2002
WO 0249540 A2 6/2002
WO WO-2003037222 A2 5/2003
WO 03047468 A1 6/2003
WO WO-2003088873 A1 10/2003
WO WO-2003096932 A1 11/2003
WO WO-2004026117 A2 4/2004
WO 2005034812 A1 4/2005
WO 2005055883 A1 6/2005
WO 2005084595 A1 9/2005
WO WO-2006005015 A2 1/2006
WO 2006014233 A2 2/2006
WO 2006032051 A2 3/2006
WO 2006034008 A2 3/2006
WO 2006111391 A1 10/2006
WO 2006127089 A1 11/2006
WO 2006138173 A2 12/2006
WO 2005102015 A3 4/2007
WO 2007047488 A2 4/2007
WO 2007067942 A1 6/2007
WO 2007097983 A2 8/2007
WO 2008005405 A2 1/2008
WO 2008015257 A2 2/2008
WO 2008033589 A1 3/2008
WO 2008035337 A2 3/2008
WO 2008091515 A2 7/2008
WO 2008147964 A1 12/2008
WO 2008150529 A1 12/2008
WO WO-2008156826 A2 12/2008
WO 2009033469 A1 3/2009
WO 2009042196 A2 4/2009
WO 2009053497 A1 4/2009
WO 2009061389 A2 5/2009
WO WO-2009094188 A2 7/2009
WO 2009116041 A2 9/2009
WO WO-2009140545 A2 11/2009
WO 2009149462 A2 12/2009
WO 2010011699 A2 1/2010
WO 2010121076 A2 10/2010
WO WO-2012023978 A2 2/2012
WO 2013106585 A1 7/2013
WO WO-2014164832 A1 10/2014
WO 2015085218 A1 6/2015
WO WO-2017099820 A2 6/2017

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

(56) References Cited

OTHER PUBLICATIONS

Wheatley, "Valve Prostheses," Operative Surgery, 4th ed. pp. 415-424. 1986.
Uchida, "Modifications of Gianturco Expandable Wire Stents," American Journal of Roentgenology, vol. 150. pp. 1185-1187. 1986.
Al Zaibag M., et al., "Percutaneous Balloon Valvotomy in Tricuspid Stenosis," British Heart Journal, Jan. 1987, vol. 57, No. 1, pp. 51-53.
Almagor M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN : 0735-1097, (Nov. 15, 1990).
Benchimol A., et al., "Simultaneous Left Ventricular Echocardiography and Aortic Blood Velocity During Rapid Right Ventricular Pacing in Man," The American Journal of the Medical Sciences, Elsevier, United States, Jan.-Feb. 1977, vol. 273, No. 1, pp. 55-62.
Dake M.D., et al., "Transluminal Placement of Endovascular Stent-Grafts for the Treatment of Descending Thoracic Aortic Aneurysms," The New England Journal of Medicine, Dec. 29, 1994, vol. 331, No. 26, pp. 1729-1734.
Dotter C.T., et al., "Transluminal Treatment of Arteriosclerotic Obstruction: Description of a New Technic and a Preliminary Report of Its Application," Circulation, Lippincott Williams & Wilkins, Philadelphia, PA, Nov. 1, 1964, vol. XXX, No. 30, pp. 654-670.
Fontaine A.B., et al., "Prototype Stent: Invivo Swine Studies in the Biliary System1", Journal of Vascular and Interventional Radiology, January-Feb. 1997, vol. 8, No. 1, pp. 101-105,.
Fontaine A.B., et al., "Vascular Stent Prototype: Results of Preclinical Evaluation," Technical Developments and Instrumentation, January-Feb. 1996, vol. 7, No. 1, pp. 29-34.
Inoue K., et al., "Clinical Application of Transvenous Mitral Commissurotomy by a New Balloon Catheter," The Journal of Thoracic and Cardiovascular Surgery, Mar. 1984, vol. 87, No. 3, pp. 394-402 (10 Pages).
Kolata G., "Device That Opens Clogged Arteries Gets a Failing Grade in a New Study", The New York Times, 03 Janurary 1991, pp. 1-2 [online], [Retrieved On Jul. 29, 2009], Retrieved from the Internet URL: http://www.nytimes.com/1991/01/03/health/device-that-opens-clogged-arteries-gets-a-faili.
Lawrence D.D(Jr)., et al., "Percutaneous Endovascular Graft: Experimental Evaluation," Cardiovascular Radiology, May 1987, vol. 163, pp. 357-360.
Pavcnik D., et al., "Development and Initial Experimental Evaluation of a Prosthetic Aortic Valve for Transcatheter Placement," Cardiovascular Radiology, Apr. 1, 1992, vol. 183(1), pp. 151-154.
Porstmann W., et al., "The Closure of the Persistent Ductus Arteriosus Ohne Thorakotomie", Thoracic Surgery Vascular Surgery, Stuttgart, Apr. 1967, vol. 15, Issue No. 2, pp. 199-203.
Rashkind W.J., et al., "Creation of an Atrial Septal Defect Without Thoracotomy: A Pallative Approach to Complete Transposition of the Great Arteries," The Journal of the American Medical Association, Jun. 13, 1966, vol. 196, No. 11, pp. 173-174 (3 Pages).
Rosch J., et al., "The Birth, Early Years and Future of Interventional Radiology," Journal of Vascular and Interventional Radiology, Jul. 2003, vol. 14, No. 7, pp. 841-853.
Ross, "Renal Ostial Stent System with Progressi-flex Technology," Evasc Medical Systems, Jun. 2009, 1 Page. (Applicant requests the Examiner to consider this reference to be prior art as of Jun. 2009).
Selby J.B., "Experience with New Retrieval Forceps for Foreign Body Removal in the Vascular, Urinary, and Biliary Systems," Radiology, Radiological Society of North America, Oak Brook, IL, Jul. 31, 1990, vol. 176, No. 2, pp. 535-538.
Serruys P.W., et al., "Stenting of Coronary Arteries. Are We the Sorcerer's Apprentice," European Heart Journal, The European Society of Cardiology, Oxford University Press, United Kingdom, Sep. 1, 1989, vol. 10, No. 9, pp. 774-782, pp. 37-45, Submitted for Publication on Jun. 13, 1989.
Serruys P.W., "Transcatheter Aortic Valve Implantation: Tips and Tricks to Avoid Failure," We File the Table of Contents and pp. 18 to 39 (Chapter 2) and pp. 102-114 (Chapter 8), the Publication Date According to the "Library of Congress Cataloging-in-Publication Data" is Nov. 24, 2009, 33 Pages.
Sigwart U., "An Overview of Intravascular Stents: Old and New," Textbook of Interventional Cardiology, Second Edition, Chapter 48, W.B. Saunders Company, Philadelphia, PA, 1994, pp. 803-815,(1990).
Urban P., "Coronary Artery Stenting", Editions Medecine et Hygiene, Geneve, 1991, pp. 5-47, ISBN: 2-88049-054-5.
Walther T., etal, "Trans-catheter Valve-in-valve Implantation: In Vitro Hydrodynamic Performance of the SAPIEN + Cloth Trans-Catheter Heart Valve in the Carpentier-Edwards Perimount Valves," European Journal of Cardio-Thoracic Surgery, 2011, vol. 40, pp. 1 120- 1126, (Sep. 23, 2010).
Watt A.H., et al., Intravenous Adenosine in the Treatment of Supraventricular Tachycardia: A Dose-ranging Study and Interaction with Dipyridamole, British Journal of Clinical Pharmacology, British Pharmacological Society, London, United Kingdom, Feb. 1986, vol. 21, No. 2, pp. 227-230.

* cited by examiner 120
110
102
100
104
114
122
118
120
136
122
110
108
112
150

102
104
126
164
130
134
168
166
104
102
126
164
134
134
130

120
110

186
168
102
188
104

120
126
112
130
114
150
134
136
122

120
110

162
168
186
188
190
192

140
134
134
130
164
126

162
102
104
166

170
110
108
128
150
154
154
112

128
112

150
154
152
154
154

170

120
138
132
136
182
174
180
178
176
122

172
172
12
106
182
180
178
176
122

182
174
180
178
176
122

122
106
154
172
154
172
112

12
136
30
32
134
120
140
106
112

122
12
30
134
32
120
140
106
136
184
112

202
18
100
104
204

202
214
16
218
110
204
212
104

300
302

218
216
236
246
220
230
224
228
234
226
244
238
120
232
242

218
216
220
222
234
228
226
120
242
240

432
434a
434c
427
434b
410
430
412
420
414
422
416
424
443
443
444
455
445
416a
445
416a
445
426

456
414
443
442
444
445
458

500
502
504
504
506
508
510
507
510
508
507

512
512
516
514
516
514
516

506
520
518

PROSTHETIC HEART VALVE

CROSS-REFERENCE TO RELATED APPLICATIONS

This application is a continuation of U.S. patent application Ser. No. 16/902,373, filed Jun. 16, 2020, which is a continuation of U.S. patent application Ser. No. 16/827,612, filed Mar. 23, 2020, which is a continuation of U.S. patent application Ser. No. 16/150,035, filed Oct. 2, 2018, now granted as U.S. Pat. No. 10,595,993, which is a division of U.S. patent application Ser. No. 14/561,102, filed Dec. 4, 2014, now granted as U.S. Pat. No. 10,098,734, which claims the benefit of U.S. Provisional Application No. 61/912,231, filed Dec. 5, 2013. Each of the foregoing applications is incorporated herein by reference.

FIELD

The present disclosure concerns embodiments of a prosthetic valve (e.g., prosthetic heart valve) and a delivery apparatus for implanting a prosthetic valve, including introducer sheaths.

BACKGROUND

Prosthetic cardiac valves have been used for many years to treat cardiac valvular disorders. The native heart valves (such as the aortic, pulmonary and mitral valves) serve critical functions in assuring the forward flow of an adequate supply of blood through the cardiovascular system. These heart valves can be rendered less effective by congenital, inflammatory, or infectious conditions. Such damage to the valves can result in serious cardiovascular compromise or death. For many years the definitive treatment for such disorders was the surgical repair or replacement of the valve during open-heart surgery, but such surgeries are prone to many complications. More recently, a transvascular technique has been developed for introducing and implanting a prosthetic heart valve using a flexible catheter in a manner that is less invasive than open heart surgery.

In this technique, a prosthetic valve is mounted in a crimped state on the end portion of a flexible catheter and advanced through a blood vessel of the patient until the prosthetic valve reaches the implantation site. The prosthetic valve at the catheter tip is then expanded to its functional size at the site of the defective native valve, such as by inflating a balloon on which the prosthetic valve is mounted. Alternatively, the prosthetic valve can have a resilient, self-expanding stent or frame that expands the prosthetic valve to its functional size when it is advanced from a delivery sheath at the distal end of the catheter.

The native valve annulus in which an expandable prosthetic valve is deployed typically has an irregular shape mainly due to calcification. As a result, small gaps may exist between the expanded frame of the prosthetic valve and the surrounding tissue. The gaps can allow for regurgitation (leaking) of blood flowing in a direction opposite the normal flow of blood through the valve. To minimize regurgitation, various sealing devices have been developed that seal the interface between the prosthetic valve and the surrounding tissue.

SUMMARY

The present disclosure is directed to embodiments of catheter-based prosthetic heart valves, and in particular, prosthetic heart valves having sealing members configured to seal the interface between the prosthetic valve and the surrounding tissue of the native annulus in which the prosthetic valve is implanted. The present disclosure also discloses new methods of making an introducer sheath with an inner liner for percutaneous insertion of a medical device into a patient.

In one representative embodiment, a prosthetic heart valve comprises a collapsible and expandable annular frame that is configured to be collapsed to a radially collapsed state for mounting on a delivery apparatus and expanded to a radially expanded state inside the body. The frame has an inflow end, an outflow end, and a longitudinal axis extending from the inflow end to the outflow end, and comprises a plurality of struts defining a plurality of rows of a plurality of cells. The prosthetic heart valve also comprises a collapsible and expandable valve member mounted within the annular frame, and a collapsible and expandable skirt assembly mounted within the annular frame. The skirt assembly comprises an upper skirt, a lower skirt, and a sealing skirt. The upper and lower skirts prevent the sealing skirt from contacting the valve member and can also couple the valve member to the annular frame. When the annular frame is expanded to its radially expanded state, portions of the sealing skirt protrude outwardly through cells of the frame.

In particular embodiments, the sealing skirt is made of loop yarn. In further embodiments, the sealing skirt is mounted within the annular frame of the prosthetic heart valve by sutures that secure the sealing skirt and the lower skirt to the frame of the prosthetic heart valve. In additional embodiments, from the longitudinal axis of the prosthetic heart valve, the valve member is positioned radially outward from the lower skirt, the upper skirt is positioned radially outward from the valve member; and the sealing skirt is positioned radially outward from the upper skirt. In more embodiments, an outflow portion of the lower skirt is sutured to an inflow portion of the valve member; and the inflow portion of the valve member is sutured to an inflow portion of the upper skirt.

In another representative embodiment, a method of making an introducer sheath with an inner liner for percutaneous insertion of a medical device into a patient is provided. The method comprises inserting a metal sleeve into a mold, inserting a polymer tube comprising a closed end and an open end into the metal sleeve, and pressurizing and heating the polymer tube to cause the polymer tube to expand against an inner surface of the metal sleeve so as to form the inner liner of the sheath.

In particular embodiments of the method, the preform cylindrical polymer tube is made of nylon-12, polyethylene, or fluorinated ethylene propylene (FEP). In further embodiments, the inner liner formed from the polymer tube has a radial wall thickness of from about 0.025 mm (about 0.001 inch) to about 0.075 mm (about 0.003 inch). In still more embodiments, the metal sleeve has a radial wall thickness of from about 0.05 mm (about 0.002 inch) to about 0.15 mm (about 0.006 inch). Pressurizing and heating the polymer tube can comprise injecting heated compressed gas into the polymer tube. Alternatively, pressurizing the polymer tube can comprise injecting compressed gas into the polymer tube and heating the polymer tube can comprise heating with a heat source separate from the pressurized gas. In several embodiments, the introducer sheath is configured for percutaneous insertion of a prosthetic heart valve through the femoral artery of the patient.

In several embodiments, the method can include forming an introducer sheath with an inner liner and an outer liner for percutaneous insertion of the medical device into the patient. In some embodiments of the method, a preform cylindrical polymer tube is used to form the outer liner. In particular embodiments, the preform cylindrical polymer tube used to form the outer liner can be made of nylon-12, polyether block amides, or polyethylene. In further embodiments, the outer liner has a radial wall thickness of from about 0.012 mm (about 0.0005 inch) to about 0.075 mm (about 0.003 inch).

The foregoing and other objects, features, and advantages of the invention will become more apparent from the following detailed description, which proceeds with reference to the accompanying drawings.

DETAILED DESCRIPTION

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached drawings may not show the various ways in which the disclosed methods, systems, and apparatus can be used in conjunction with other systems, methods, and apparatus.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B", "C", "A and B", "A and C", "B and C", or "A, B, and C".

As used herein, the term "coupled" generally means physically coupled or linked and does not exclude the presence of intermediate elements between the coupled items absent specific contrary language.

Figures 1, 2:
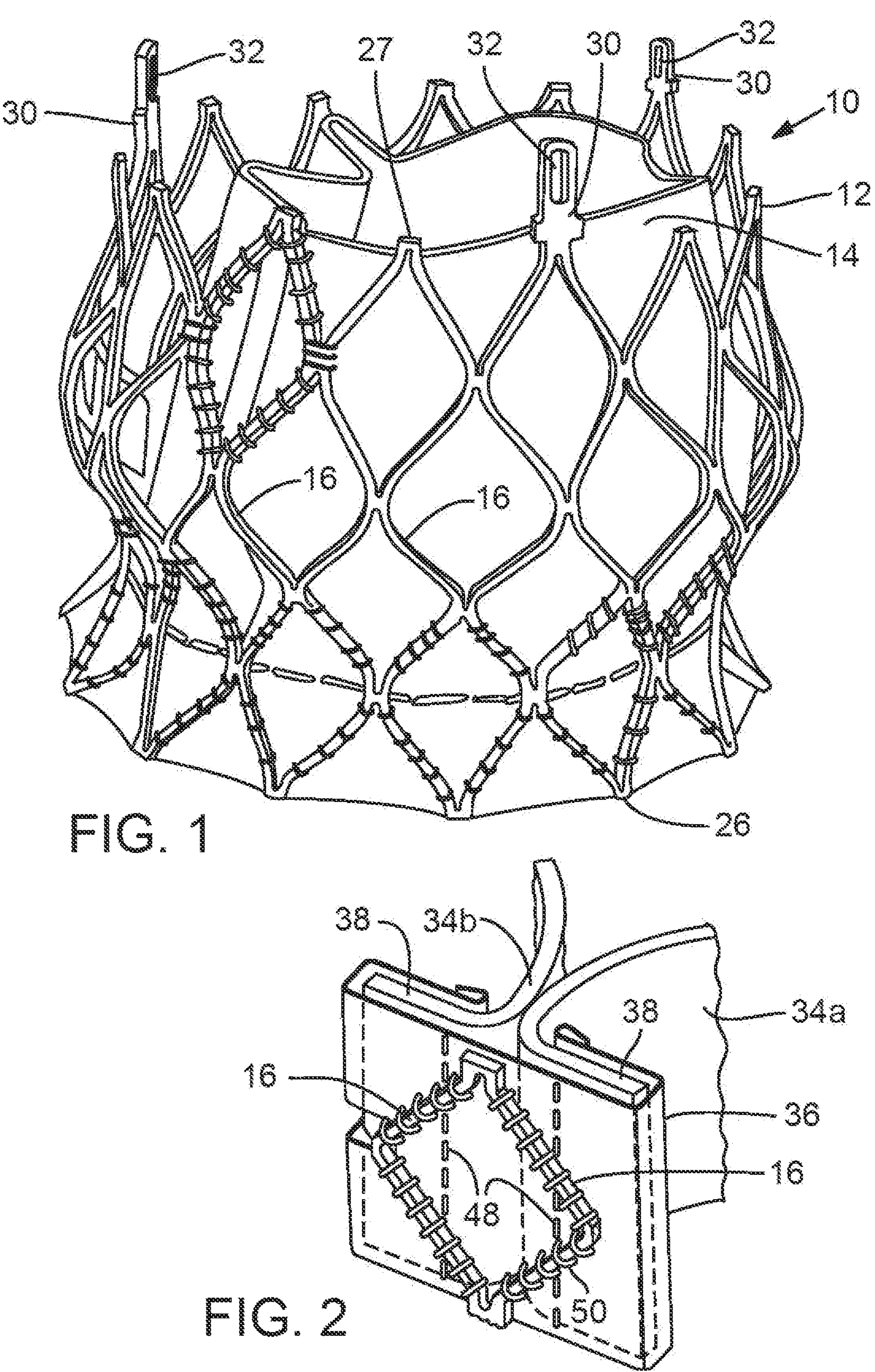
FIG. 1 is a perspective view of a prosthetic valve that can be used to replace the native aortic valve of the heart, according to one embodiment.
FIG. 2 is a perspective view of a portion of the prosthetic valve of FIG. 1 illustrating the connection of two leaflets to the support frame of the prosthetic valve.

Referring first to FIG. 1, there is shown a prosthetic aortic heart valve 10, according to one embodiment. The prosthetic valve 10 includes an expandable frame member, or stent, 12 that supports an expandable valve member, which in the illustrated embodiment comprises a flexible leaflet section 14. The prosthetic valve 10 is radially compressible to a compressed state for delivery through the body to a deployment site and expandable to its functional size shown in FIG. 1 at the deployment site. In certain embodiments, the prosthetic valve 10 is self-expanding; that is, the prosthetic valve can radially expand to its functional size when advanced from the distal end of a delivery sheath. Apparatuses particularly suited for percutaneous delivery and implantation of a self-expanding prosthetic valve are described in detail below. In other embodiments, the prosthetic valve can be a balloon-expandable prosthetic valve that can be adapted to be mounted in a compressed state on the balloon of a delivery catheter. The prosthetic valve can be expanded to its functional size at a deployment site by inflating the balloon, as known in the art.

The illustrated prosthetic valve 10 is adapted to be deployed in the native aortic annulus, although it also can be used to replace the other native valves of the heart (the mitral, tricuspid, and pulmonary valves). Moreover, the prosthetic valve 10 can be adapted to replace other valves within the body, such venous valves.

Figure 3:
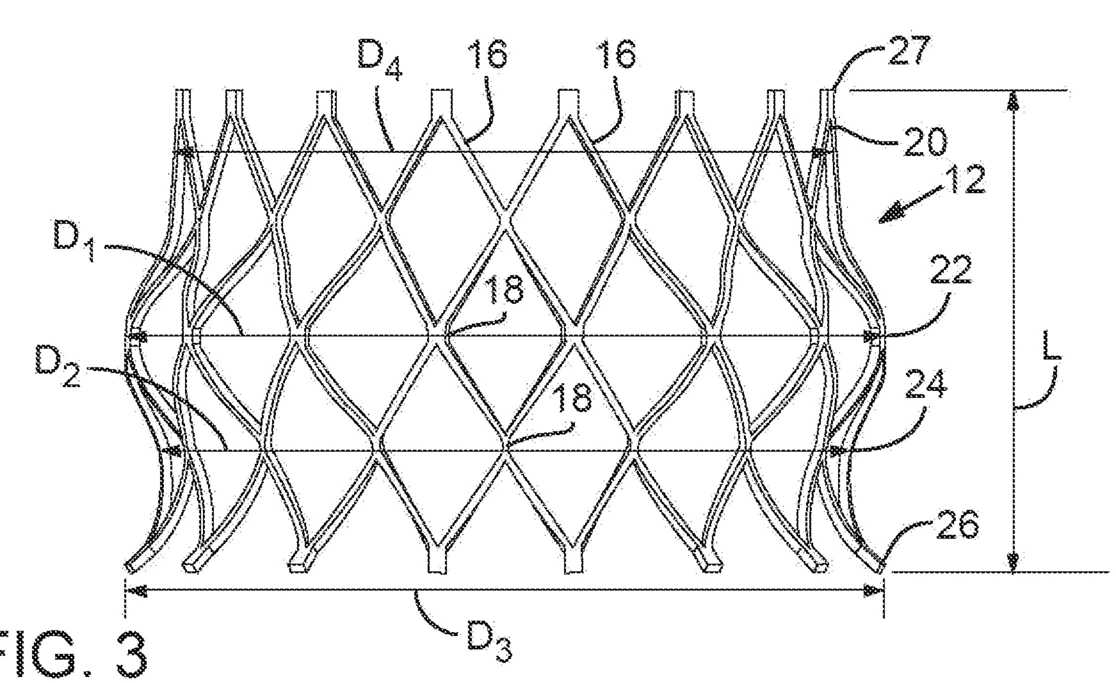
FIG. 3 is side elevation view of the support frame of the prosthetic valve of FIG. 1.
Figure 4:
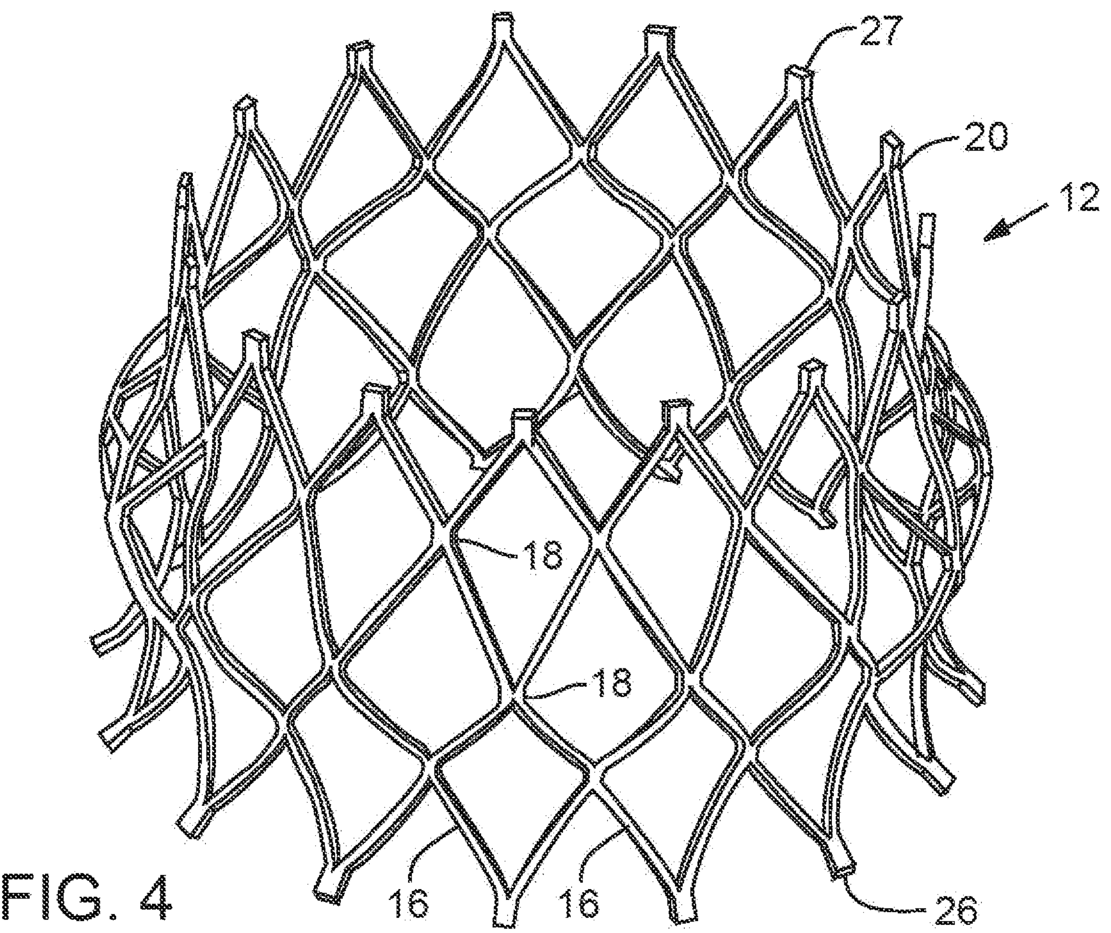
FIG. 4 is a perspective view of the support frame of the prosthetic valve of FIG. 1.

FIGS. 3 and 4 show the stent 12 without the leaflet section 14 for purposes of illustration. As shown, the stent 12 can be formed from a plurality of longitudinally extending, generally sinusoidal-shaped frame members, or struts, 16. The struts 16 are formed with alternating bends and are welded or otherwise secured to each other at nodes 18 formed from the vertices of adjacent bends so as to form a mesh structure. The struts 16 can be made of a suitable shape memory material, such as the nickel titanium alloy known as Nitinol, that allows the prosthetic valve to be compressed to a reduced diameter for delivery in a delivery apparatus (such as described below) and then causes the prosthetic valve to expand to its functional size inside the patient's body when deployed from the delivery apparatus. If the prosthetic valve is a balloon-expandable prosthetic valve that is adapted to be crimped onto an inflatable balloon of a delivery apparatus and expanded to its functional size by inflation of the balloon, the stent 12 can be made of a suitable ductile material, such as stainless steel.

The stent 12 has an inflow end 26 and an outflow end 27. The mesh structure formed by struts 16 comprises a generally cylindrical "upper" or outflow end portion 20, an outwardly bowed or distended intermediate section 22, and an inwardly bowed "lower" or inflow end portion 24. The intermediate section 22 desirably is sized and shaped to extend into the sinuses of Valsalva in the aortic root to assist in anchoring the prosthetic valve in place once implanted. As shown, the mesh structure desirably has a curved shape along its entire length that gradually increases in diameter from the outflow end portion 20 to the intermediate section 22, then gradually decreases in diameter from the intermediate section 22 to a location on the inflow end portion 24, and then gradually increases in diameter to form a flared portion terminating at the inflow end 26.

Figure 5A:
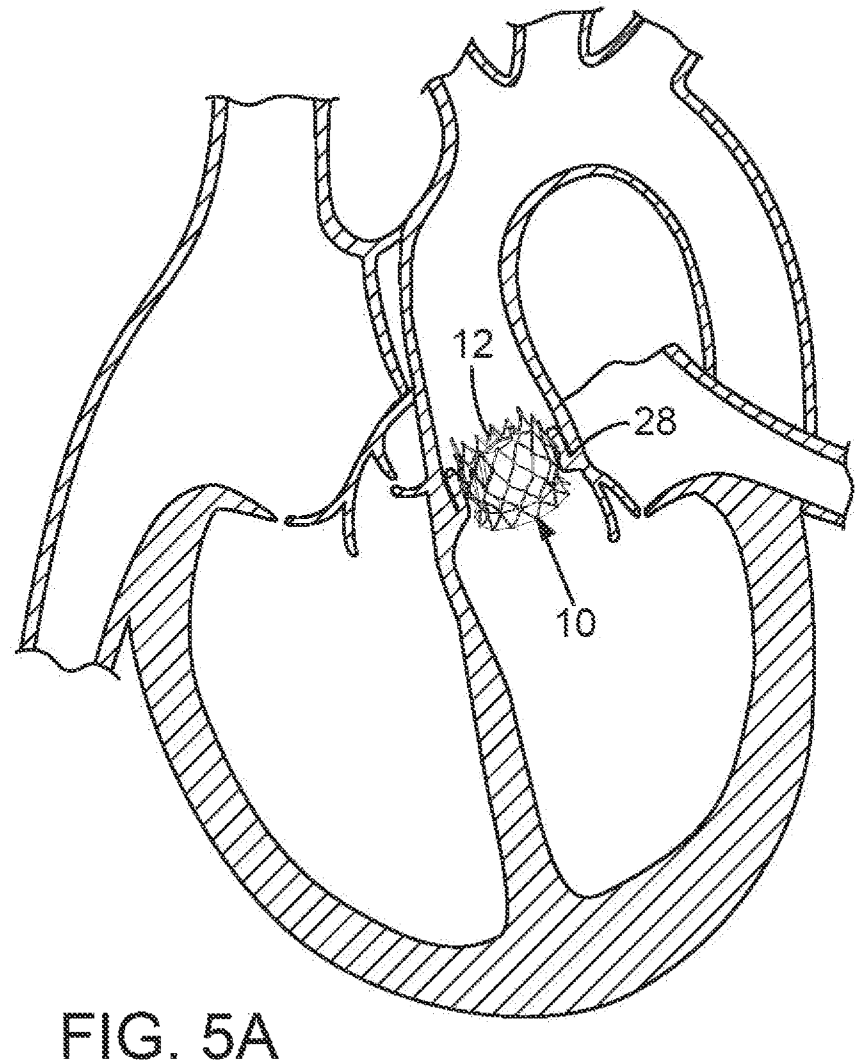
FIG. 5A is a cross-sectional view of the heart showing the prosthetic valve of FIG. 1 implanted within the aortic annulus.
Figure 5B:
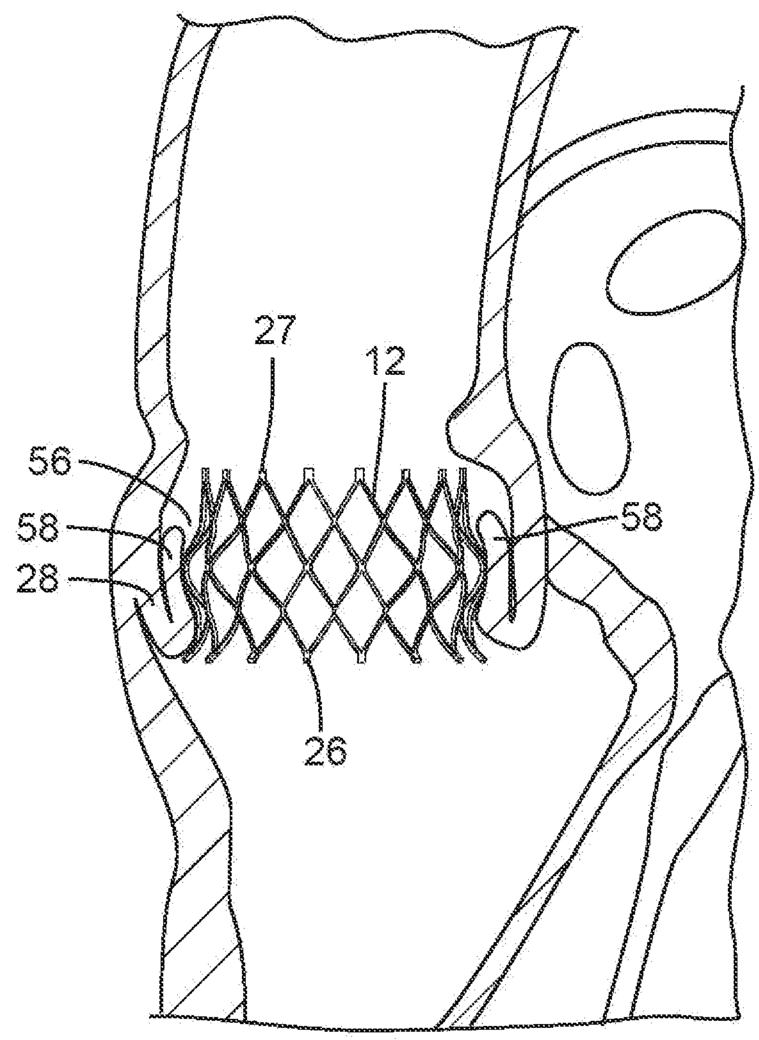
FIG. 5B is an enlarged view of FIG. 5A illustrating the prosthetic valve implanted within the aortic annulus, shown with the leaflet structure of the prosthetic valve removed for clarity.

When the prosthetic valve is in its expanded state, the intermediate section 22 has a diameter $D_1$, the inflow end portion lower section 24 has a minimum diameter $D_2$, the inflow end 26 has a diameter $D_3$, and the outflow end portion 20 has a diameter $D_4$, where $D_2$ is less than $D_1$ and $D_3$, and $D_4$ is less than $D_2$. In addition, $D_1$ and $D_3$ desirably are greater than the diameter of the native annulus in which the prosthetic valve is to be implanted. In this manner, the overall shape of the stent 12 assists in retaining the prosthetic valve at the implantation site. More specifically, and referring to FIGS. 5A and 5B, the prosthetic valve 10 can be implanted within a native valve (the aortic valve in the illustrated example) such that the lower section 24 is positioned within the aortic annulus 28, the intermediate section 22 extends above the aortic annulus into the sinuses of Valsalva 56, and the lower flared end 26 extends below the aortic annulus. The prosthetic valve 10 is retained within the native valve by the radial outward force of the lower section 24 against the surrounding tissue of the aortic annulus 28 as well as the geometry of the stent. Specifically, the intermediate section 22 and the flared lower end 26 extend radially outwardly beyond the aortic annulus 28 to better resist against axial dislodgement of the prosthetic valve in the downstream and upstream directions (toward and away from the aorta). Depending on the condition of the native leaflets 58, the prosthetic valve typically is deployed within the native annulus 28 with the native leaflets 58 folded upwardly and compressed between the outer surface of the stent 12 and the walls of the sinuses of Valsalva 56, as depicted in FIG. 5B. In some cases, it may be desirable to excise the leaflets 58 prior to implanting the prosthetic valve 10.

Known prosthetic valves having a self-expanding frame typically have additional anchoring devices or frame portions that extend into and become fixed to non-diseased areas of the vasculature. Because the shape of the stent 12 assists in retaining the prosthetic valve, additional anchoring devices are not required and the overall length L of the stent can be minimized to prevent the stent upper portion 20 from extending into the non-diseased area of the aorta, or to at least minimize the extent to which the upper portion 20 extends into the non-diseased area of the aorta. Avoiding the non-diseased area of the patient's vasculature helps avoid complications if future intervention is required. For example, the prosthetic valve can be more easily removed from the patient because the stent is primarily anchored to the diseased part of the native valve. Furthermore, a shorter prosthetic valve is more easily navigated around the aortic arch.

In particular embodiments, for a prosthetic valve intended for use in a 22-mm to 24-mm annulus, the diameter D1 is from about 28 mm to about 32 mm, with about 30 mm being a specific example; the diameter D2 is from about 24 mm to about 28 mm, with about 26 mm being a specific example; the diameter D3 is from about 28 mm to about 32 mm, with about 30 mm being a specific example; and the diameter D4 is from about 24 mm to about 28 mm, with about 26 mm being a specific example. The length L in particular embodiments is from about 20 mm to about 24 mm, with about 22 mm being a specific example.

Referring to FIG. 1, the stent 12 can have a plurality of angularly spaced retaining arms, or projections, in the form of posts 30 (three in the illustrated embodiment) that extend from the stent upper portion 20. Each retaining arm 30 has a respective aperture 32 that is sized to receive prongs of a valve-retaining mechanism that can be used to form a releasable connection between the prosthetic valve and a delivery apparatus (described below). In alternative embodiments, the retaining arms 30 need not be provided if a valve-retaining mechanism is not used.

Figures 6, 7:
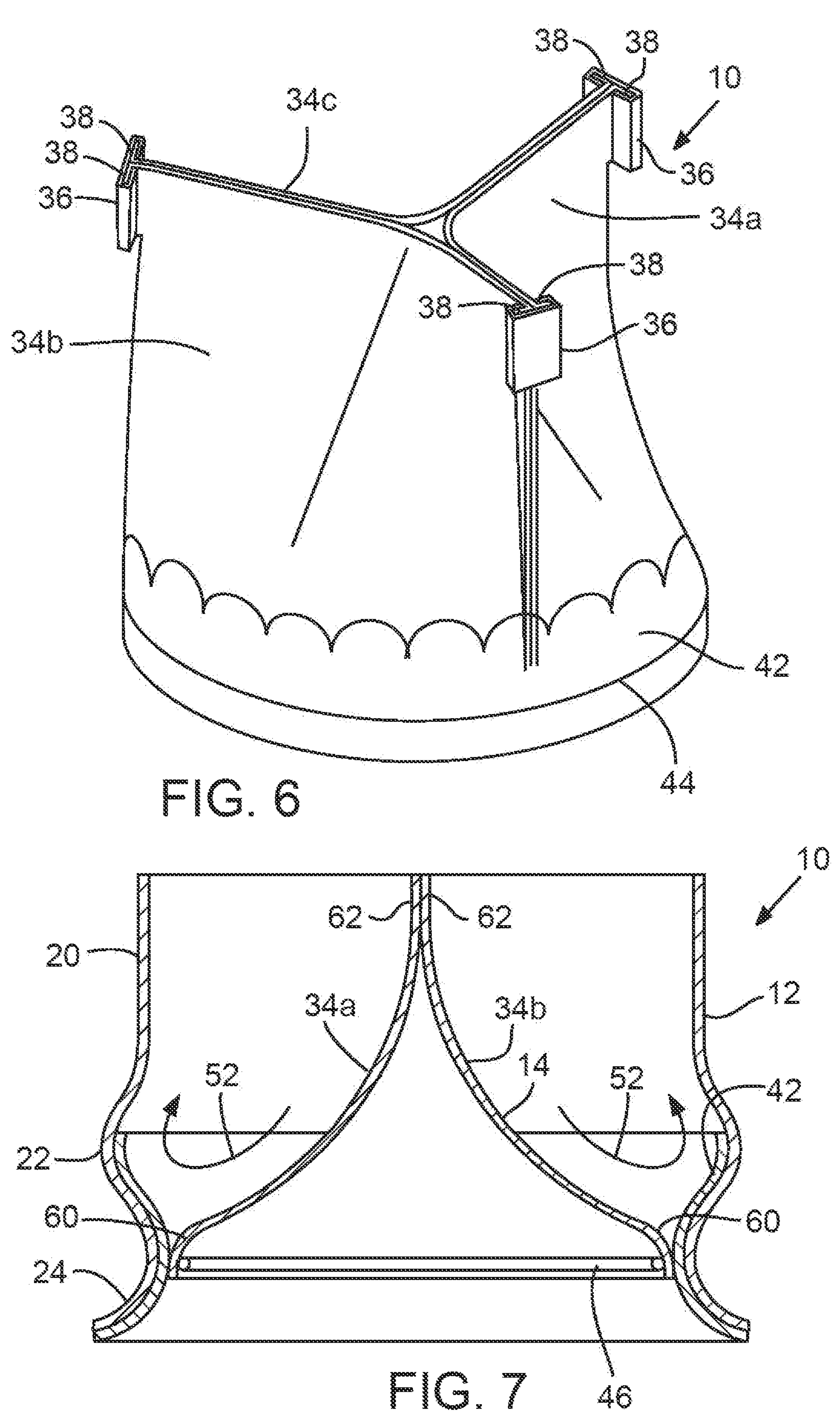
FIG. 6 is a perspective view of the leaflet structure of the prosthetic valve of FIG. 1 shown prior to being secured to the support frame.
FIG. 7 is a cross-sectional view of the prosthetic valve of FIG. 1.

As best shown in FIGS. 6 and 7, the leaflet assembly 14 in the illustrated embodiment comprises three leaflets 34*a*, 34*b*, 34*c* made of a flexible material. Each leaflet has an inflow end portion 60 and an outflow end portion 62. The leaflets can comprise any suitable biological material (e.g., pericardial tissue, such as bovine or equine pericardium), bio-compatible synthetic materials, or other such materials, such as those described in U.S. Pat. No. 6,730,118, which is incorporated herein by reference. The leaflet assembly 14 can include an annular reinforcing skirt 42 that is secured to the inflow end portions of the leaflets 34*a*, 34*b*, 34*c* at a suture line 44 adjacent the inflow end of the prosthetic valve. The inflow end portion of the leaflet assembly 14 can be secured to the stent 12 by suturing the skirt 42 to struts 16 of the lower section 24 of the stent (best shown in FIG. 1). As shown in FIG. 7, the leaflet assembly 14 can further include an inner reinforcing strip 46 that is secured to the inner surfaces of the inflow end portions 60 of the leaflets.

Referring to FIGS. 1 and 2, the outflow end portion of the leaflet assembly 14 can be secured to the upper portion of the stent 12 at three angularly spaced commissure attachments of the leaflets 34*a*, 34*b*, and 34*c*. As best shown in FIG. 2, each commissure attachment can be formed by wrapping a reinforcing section 36 around adjacent upper edge portions 38 of a pair of leaflets at the commissure formed by the two leaflets and securing the reinforcing section 36 to the edge portions 38 with sutures 48. The sandwiched layers of the reinforcing material and leaflets can then be secured to the struts 16 of the stent 12 with sutures 50 adjacent the outflow end of the stent. The leaflets therefore desirably extend the entire length or substantially the entire length of the stent from the inflow end 26 to the outflow end 27. The reinforcing sections 36 reinforces the attachment of the leaflets to the stent so as to minimize stress concentrations at the suture lines and avoid "needle holes" on the portions of the leaflets that flex during use. The reinforcing sections 36, the skirt 42, and the inner reinforcing strip 46 (FIG. 7) desirably are made of a bio-compatible synthetic material, such as polytetrafluoroethylene (PTFE), or a woven fabric material, such as woven polyester (e.g., polyethylene terephthalate) (PET), DACRON®).

FIG. 7 shows the operation of the prosthetic valve 10. During diastole, the leaflets 34*a*, 34*b*, 34*c* collapse to effectively close the prosthetic valve. As shown, the curved shape of the intermediate section 22 of the stent 12 defines a space between the intermediate section and the leaflets that mimics the sinuses of Valsalva. Thus, when the leaflets close, backflow entering the "sinuses" creates a turbulent flow of blood along the upper surfaces of the leaflets, as indicated by arrows 52. This turbulence assists in washing the leaflets and the skirt 42 to minimize or reduce clot formation.

The prosthetic valve 10 can be implanted in a retrograde approach where the prosthetic valve, mounted in a crimped state at the distal end of a delivery apparatus, is introduced into the body via the femoral artery and advanced through the aortic arch to the heart, as further described in U.S. Patent Application Publication No. 2008/0065011, which is incorporated herein by reference.

Figures 8, 9, 10:
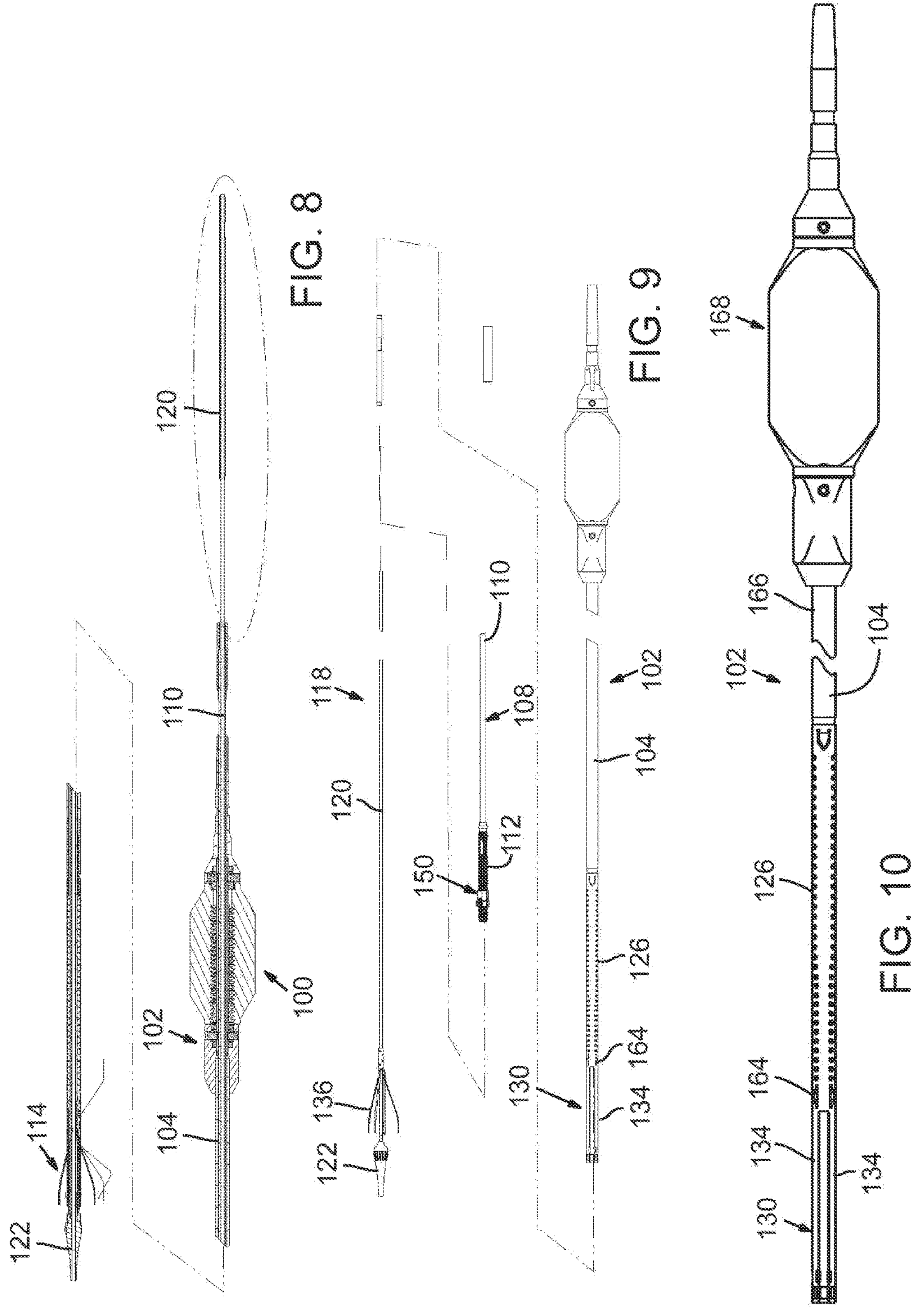
FIG. 8 is a cross-sectional view of an embodiment of a delivery apparatus that can be used to deliver and implant a prosthetic valve, such as the prosthetic valve shown in FIG. 1.
FIG. 9 is an exploded view of the delivery apparatus of FIG. 8.
FIG. 10 is a side view of the guide catheter of the delivery apparatus of FIG. 8.

FIGS. 8 and 9 show a delivery apparatus 100, according to one embodiment, that can be used to deliver a self-expanding prosthetic valve, such as prosthetic valve 10 described above, through a patient's vasculature. The delivery apparatus 100 comprises a first, outermost or main catheter 102 (shown alone in FIG. 10) having an elongated shaft 104, the distal end of which is coupled to a delivery sheath 106 (FIG. 18; also referred to as a delivery cylinder). The proximal end of the main catheter 102 is connected to a handle of the delivery apparatus. FIGS. 23-26 show an embodiment of a handle mechanism having an electric motor for operating the delivery apparatus. The handle mechanism is described in detail below. During delivery of a prosthetic valve, the handle can be used by a surgeon to advance and retract the delivery apparatus through the patient's vasculature. Although not required, the main catheter 102 can comprise a guide catheter that is configured to allow a surgeon to guide or control the amount the bending or flexing of a distal portion of the shaft 104 as it is advanced through the patient's vasculature, such as further described below. Another embodiment of a guide catheter is disclosed in U.S. Patent Application Publication No. 2008/0065011, which is incorporated herein by reference.

As best shown in FIG. 9, the delivery apparatus 100 also includes a second, intermediate catheter 108 (also referred to herein as a torque shaft catheter) having an elongated shaft 110 (also referred to herein as a torque shaft) and an elongated screw 112 connected to the distal end of the shaft 110. The shaft 110 of the intermediate catheter 108 extends coaxially through the shaft 104 of the main catheter 102. The delivery apparatus 100 can also include a third, nose-cone catheter 118 having an elongated shaft 120 and a nose piece, or nose cone, 122 secured to the distal end portion of the shaft 120. The nose piece 122 can have a tapered outer surface as shown for atraumatic tracking through the patient's vasculature. The shaft 120 of the nose-cone catheter extends through the prosthetic valve 10 (not shown in FIGS. 8-9) and the shaft 110 of the intermediate catheter 108. In the illustrated configuration, the innermost shaft 120 is configured to be moveable axially and rotatably relative to the shafts 104, 110, and the torque shaft 110 is configured to be rotatable relative to the shafts 104, 120 to effect valve deployment and release of the prosthetic valve from the delivery apparatus, as described in detail below. Additionally, the innermost shaft 120 can have a lumen for receiving a guide wire so that the delivery apparatus can be advanced over the guide wire inside the patient's vasculature.

As best shown in FIG. 10, the outer catheter 102 can comprise a flex control mechanism 168 at a proximal end thereof to control the amount the bending or flexing of a distal portion of the outer shaft 104 as it is advanced through the patient's vasculature, such as further described below. The outer shaft 104 can comprise a proximal segment 166 that extends from the flex control mechanism 168 and a distal segment 126 that comprises a slotted metal tube that increases the flexibility of the outer shaft at this location. The distal end portion of the distal segment 126 can comprises an outer fork 130 of a valve-retaining mechanism 114 (FIGS. 8 and 8B) that is configured to releasably secure a prosthetic valve 10 to the delivery apparatus 100 during valve delivery, as described in detail below.

Figures 11, 12:
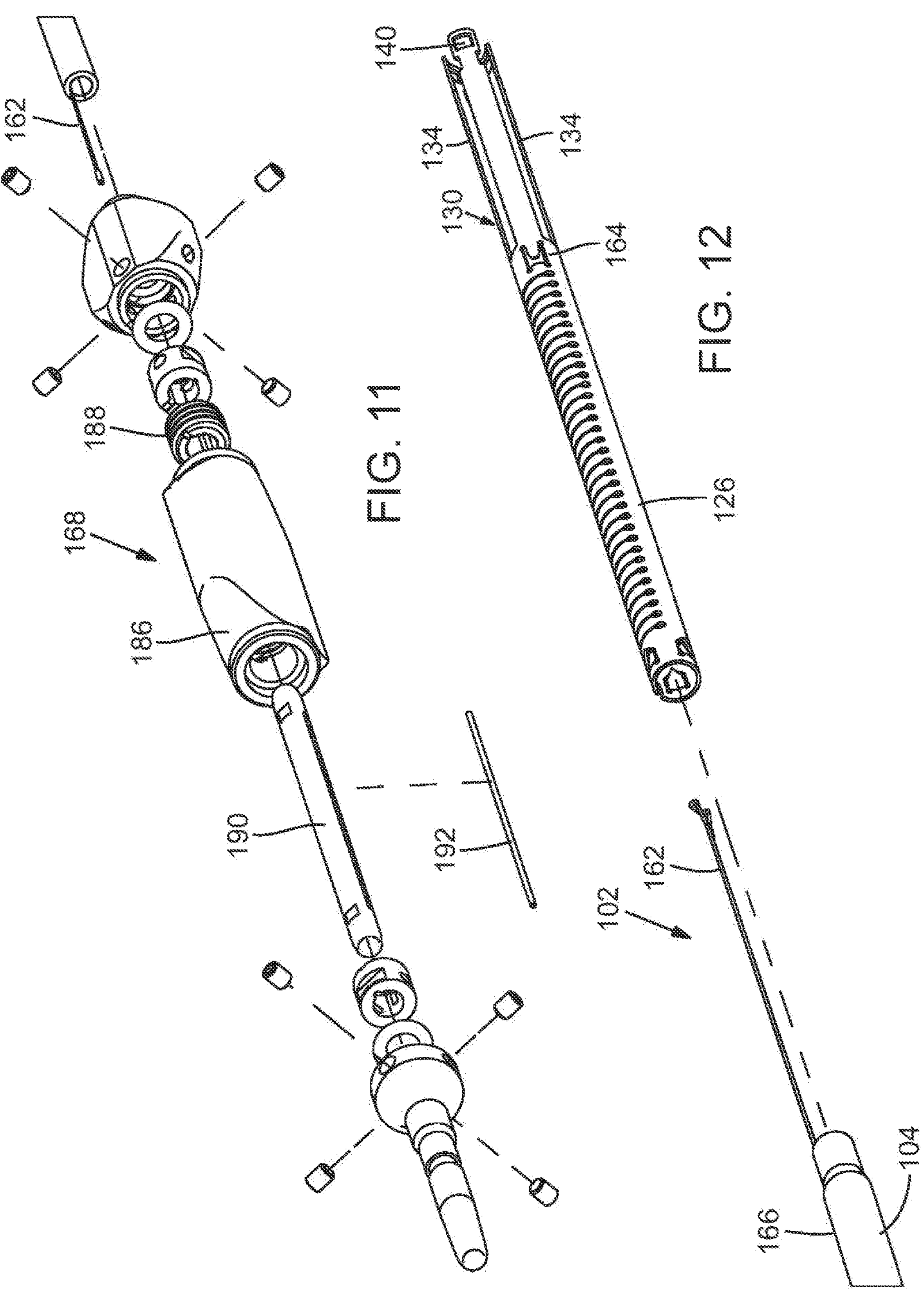
FIG. 11 is a perspective, exploded view of the proximal end portion of the guide catheter of FIG. 10.
FIG. 12 is a perspective, exploded view of the distal end portion of the guide catheter of FIG. 10.
Figure 28A:
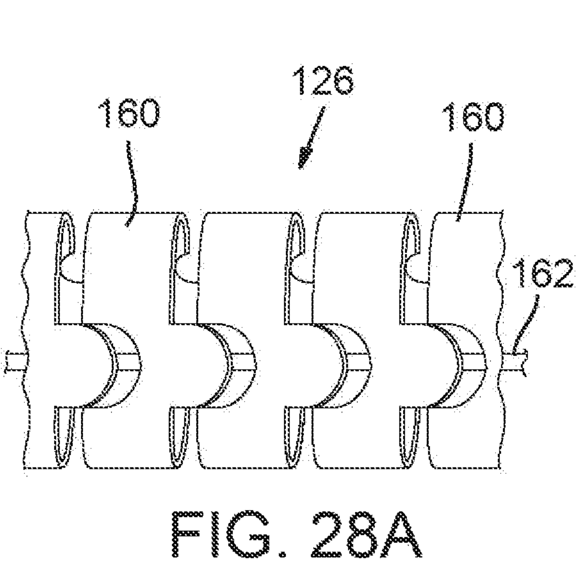
FIG. 28A is an enlarged view of a distal segment of the guide catheter shaft of FIG. 10.
Figure 28B:
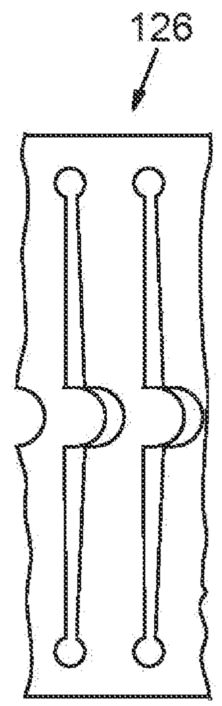
FIG. 28B shows the cut pattern for forming the portion of the shaft shown in FIG. 28A, such as by laser cutting a metal tube.

FIG. 28A is an enlarged view of a portion of the distal segment 126 of the outer shaft 104. FIG. 28B shows the cut pattern that can be used to form the distal segment 126 by laser cutting the pattern in a metal tube. The distal segment 126 comprises a plurality of interconnected circular bands or links 160 forming a slotted metal tube. A pull wire 162 can be positioned inside the distal segment 126 and can extend from a location 164 of the distal segment 126 (FIGS. 10 and 12) to the flex control mechanism. The distal end of the pull wire 162 can be secured to the inner surface of the distal segment 126 at location 164, such as by welding. The proximal end of the pull wire 162 can be operatively connected to the flex control mechanism 168, which is configured to apply and release tension to the pull wire in order to control bending of the shaft, as further described below. The links 160 of the shaft and the gaps between adjacent links are shaped to allow bending of the shaft upon application of light pulling force on the pull wire 162. In the illustrated embodiment, as best shown in FIG. 12, the distal segment 126 is secured to a proximal segment 166 having a different construction (e.g., one or more layers of polymeric tubing). In the illustrated embodiment, the proximal segment 166 extends from the flex control mechanism 168 to the distal segment 126 and therefore makes up the majority of the length of the outer shaft 104. In alternative embodiments, the entire length or substantially the entire length of the outer shaft 104 can be formed from a slotted metal tube comprising one or more sections of interconnected links 160. In any case, the use of a main shaft having such a construction can allow the delivery apparatus to be highly steerable.

The width of the links 160 can be varied to vary the flexibility of the distal segment along its length. For example, the links within the distal end portion of the slotted tube can be relatively narrower to increase the flexibility of the shaft at that location while the links within the proximal end portion of the slotted tube can be relatively wider so that the shaft is relatively less flexible at that location.

Figure 29A:
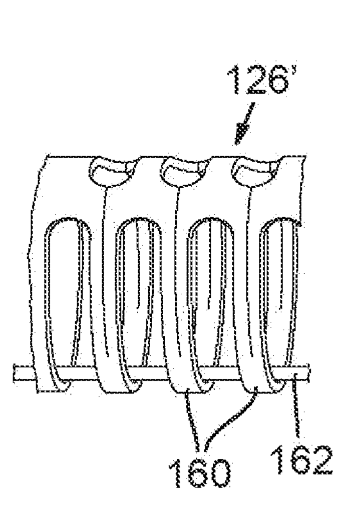
FIG. 29A is an enlarged view of a distal segment of a guide catheter shaft, according to another embodiment.
Figure 29B:
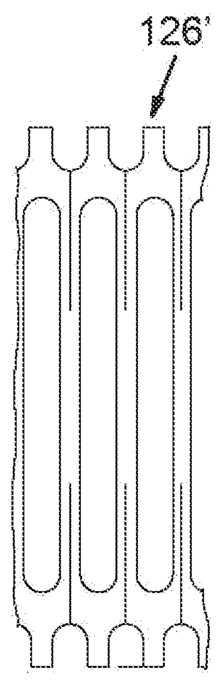
FIG. 29B shows the cut pattern for forming the shaft of FIG. 29A, such as by laser cutting a metal tube.

FIG. 29A shows an alternative embodiment of a distal segment, indicated at 126', which can be formed, for example, by laser cutting a metal tube. The segment 126' can comprise the distal segment of an outer shaft of a delivery apparatus (as shown in FIG. 12) or substantially the entire length of an outer shaft can have the construction shown in FIG. 29A. FIG. 29B shows the cut pattern for forming the segment 126'. In another embodiment, a delivery apparatus can include a composite outer shaft comprising a laser-cut metal tube laminated with a polymeric outer layer that is fused within the gaps in the metal layer. In one example, a composite shaft can comprise a laser cut metal tube having the cut pattern of FIGS. 29A and 29B and a polymeric outer layer fused in the gaps between the links 160 of the metal tube. In another example, a composite shaft can comprise a laser cut metal tube having the cut pattern of FIGS. 28A and 28B and a polymeric outer layer fused in the gaps between the links 160 of the metal tube. A composite shaft also can include a polymeric inner layer fused in the gaps between the links 160 of the metal tube.

Figures 8A, 8B, 8C:
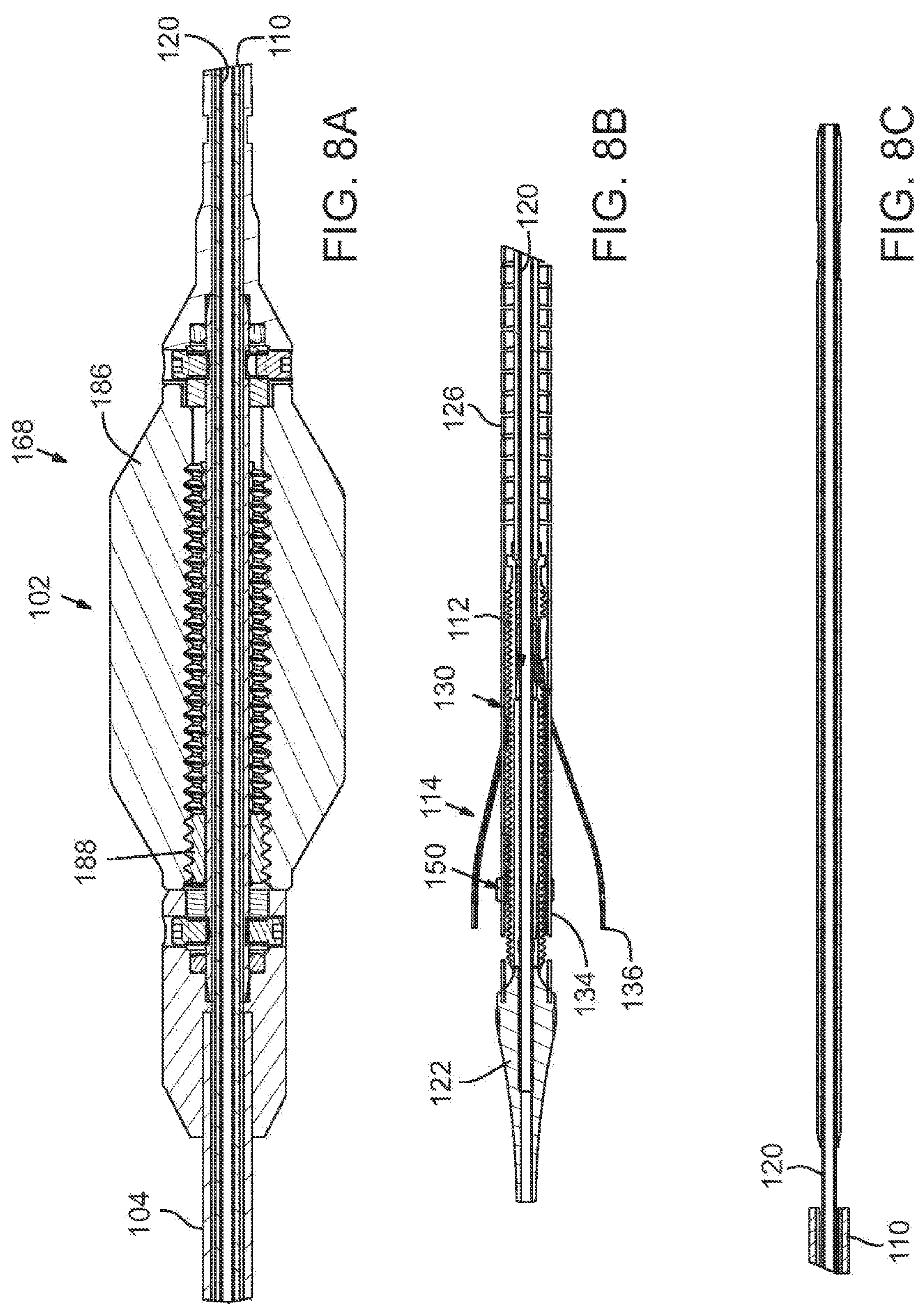
FIGS. 8A-8C are enlarged cross-sectional views of sections of FIG. 8.

Referring to FIGS. 8A and 11, the flex control mechanism 168 can comprise a rotatable housing, or handle portion, 186 that houses a slide nut 188 mounted on a rail 192. The slide nut 188 is prevented from rotating within the housing by one or more rods 192, each of which is partially disposed in a corresponding recess within the rail 192 and a slot or recess on the inside of the nut 188. The proximal end of the pull wire 162 is secured to the nut 188. The nut 188 has external threads that engage internal threads of the housing. Thus, rotating the housing 186 causes the nut 188 to move axially within the housing in the proximal or distal direction, depending on the direction of rotation of the housing. Rotating the housing in a first direction (e.g., clockwise), causes the nut to travel in the proximal direction, which applies tension to the pull wire 162, which causes the distal end of the delivery apparatus to bend or flex. Rotating the housing in a second direction (e.g., counterclockwise), causes the nut to travel in the distal direction, which relieves tension in the pull wire 162 and allows the distal end of the delivery apparatus to flex back to its pre-flexed configuration under its own resiliency.

Figures 13, 14, 15, 16:
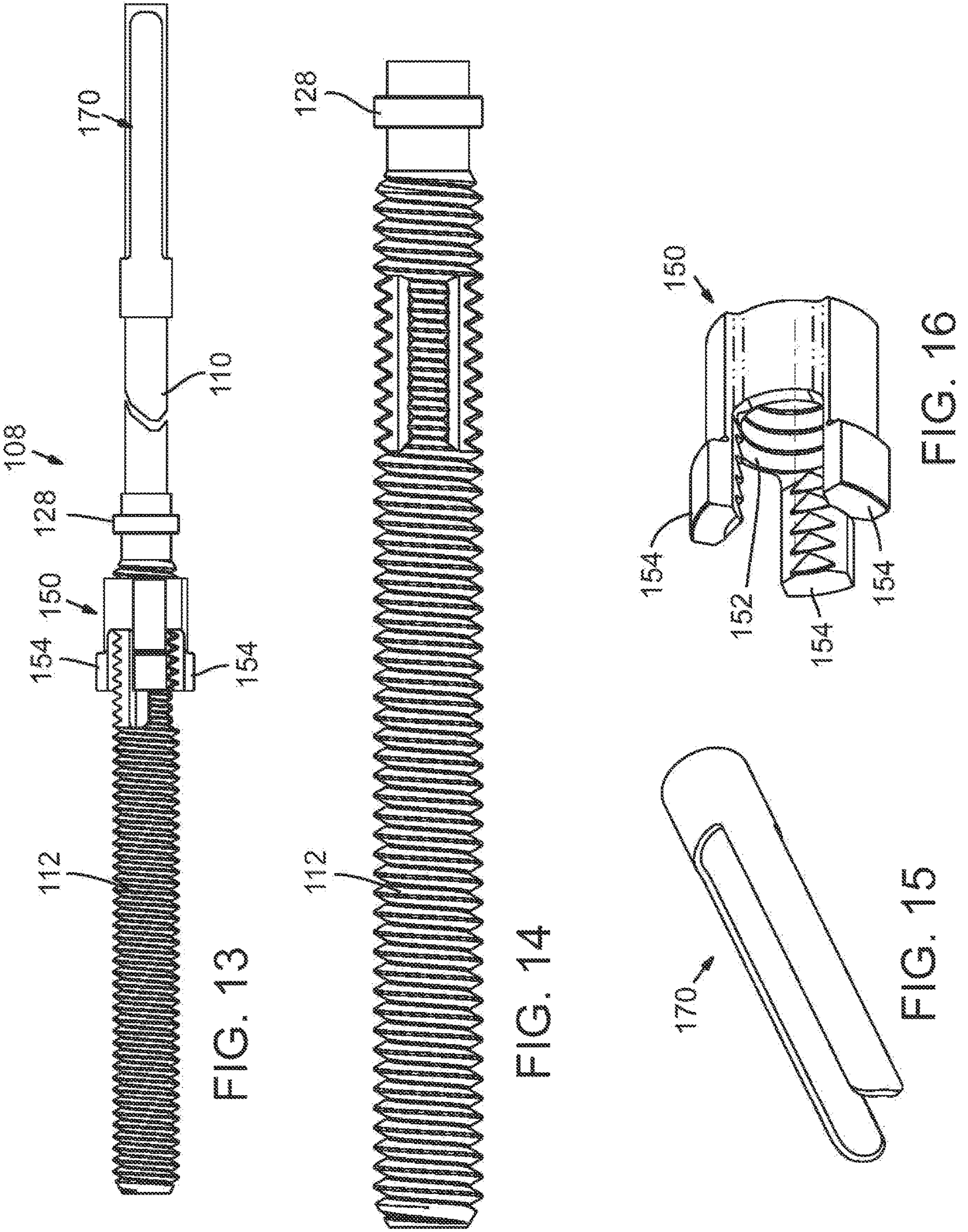
FIG. 13 is a side view of the torque shaft catheter of the delivery apparatus of FIG. 8.
FIG. 14 is an enlarged side view of the rotatable screw of the torque shaft catheter of FIG. 13.
FIG. 15 is an enlarged perspective view of a coupling member disposed at the end of the torque shaft.
FIG. 16 is an enlarged perspective view of the threaded nut used in the torque shaft catheter of FIG. 13.

As best shown in FIG. 13, the torque shaft catheter 108 includes an annular projection in the form of a ring 128 (also referred to as an anchoring disc) mounted on the distal end portion of the torque shaft 110 adjacent the screw 112. The ring 128 is secured to the outer surface of the torque shaft 110 such that it cannot move axially or rotationally relative to the torque shaft. The inner surface of the outer shaft 104 is formed with a feature, such as a slot or recess, that receives the ring 128 in such a manner that the ring and the corresponding feature on the inner surface of the outer shaft 104 allow the torque shaft 110 to rotate relative to the outer shaft 104 but prevent the torque shaft from moving axially relative to the outer shaft. The corresponding feature on the outer shaft 104 that receives the ring 128 can be inwardly extending tab portions formed in the distal segment 126, such as shown at 164 in FIG. 12. In the illustrated embodiment (as best shown in FIG. 14), the ring 128 is an integral part of the screw 112 (i.e., the screw 112 and the ring 128 are portions of single component). Alternatively, the screw 112 and the ring are separately formed components but are both fixedly secured to the distal end of the torque shaft 110.

Figures 17, 17A, 17B:
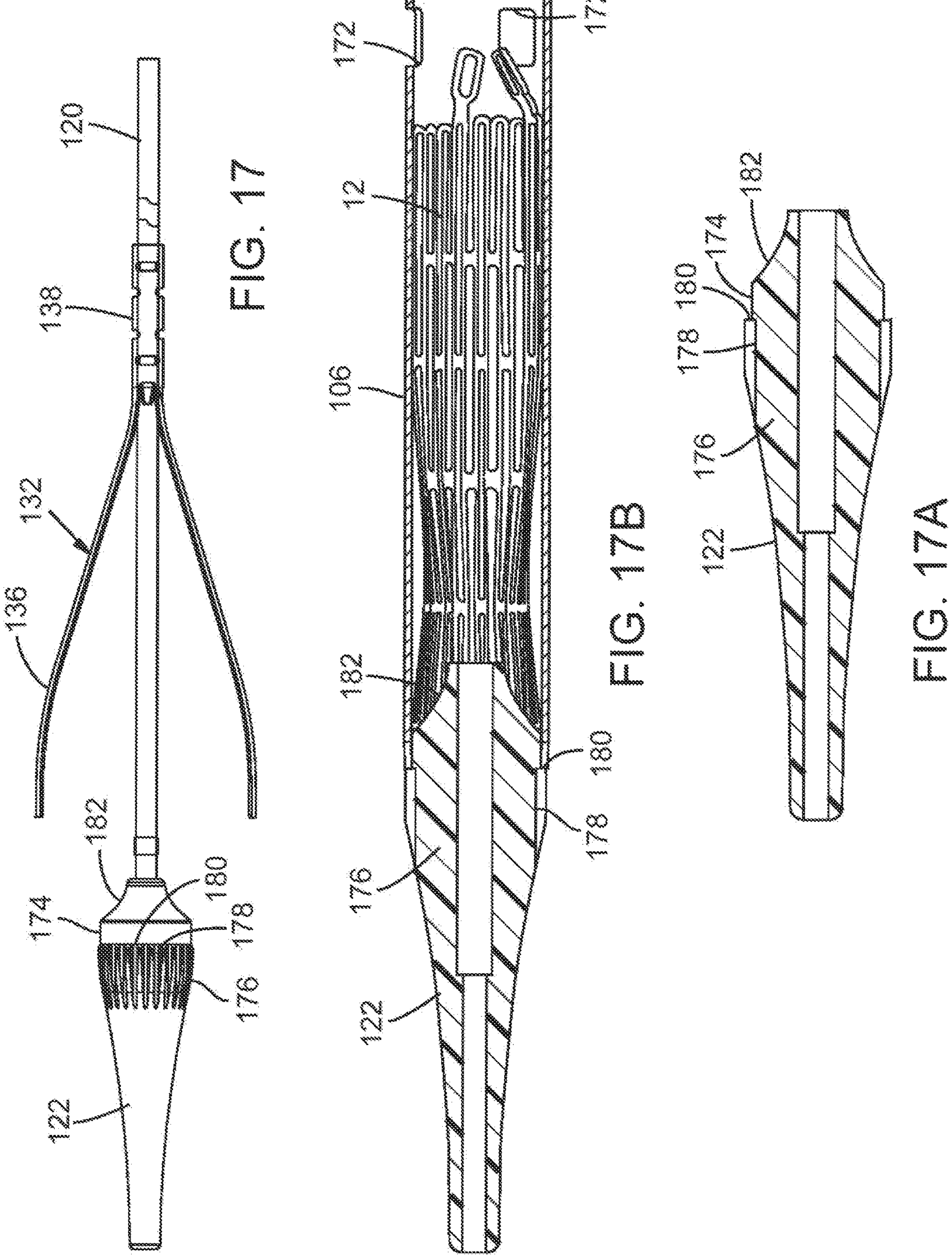
FIG. 17 is an enlarged side view of the distal end portion of the nose cone catheter of the delivery apparatus of FIG. 8.
FIG. 17A is an enlarged, cross-sectional view of the nose cone of the catheter shown FIG. 17.
FIG. 17B is an enlarged cross-sectional view of the distal end portion of the delivery apparatus of FIG. 8 showing the stent of a prosthetic valve retained in a compressed state within a delivery sheath.
Figures 18, 19, 20:
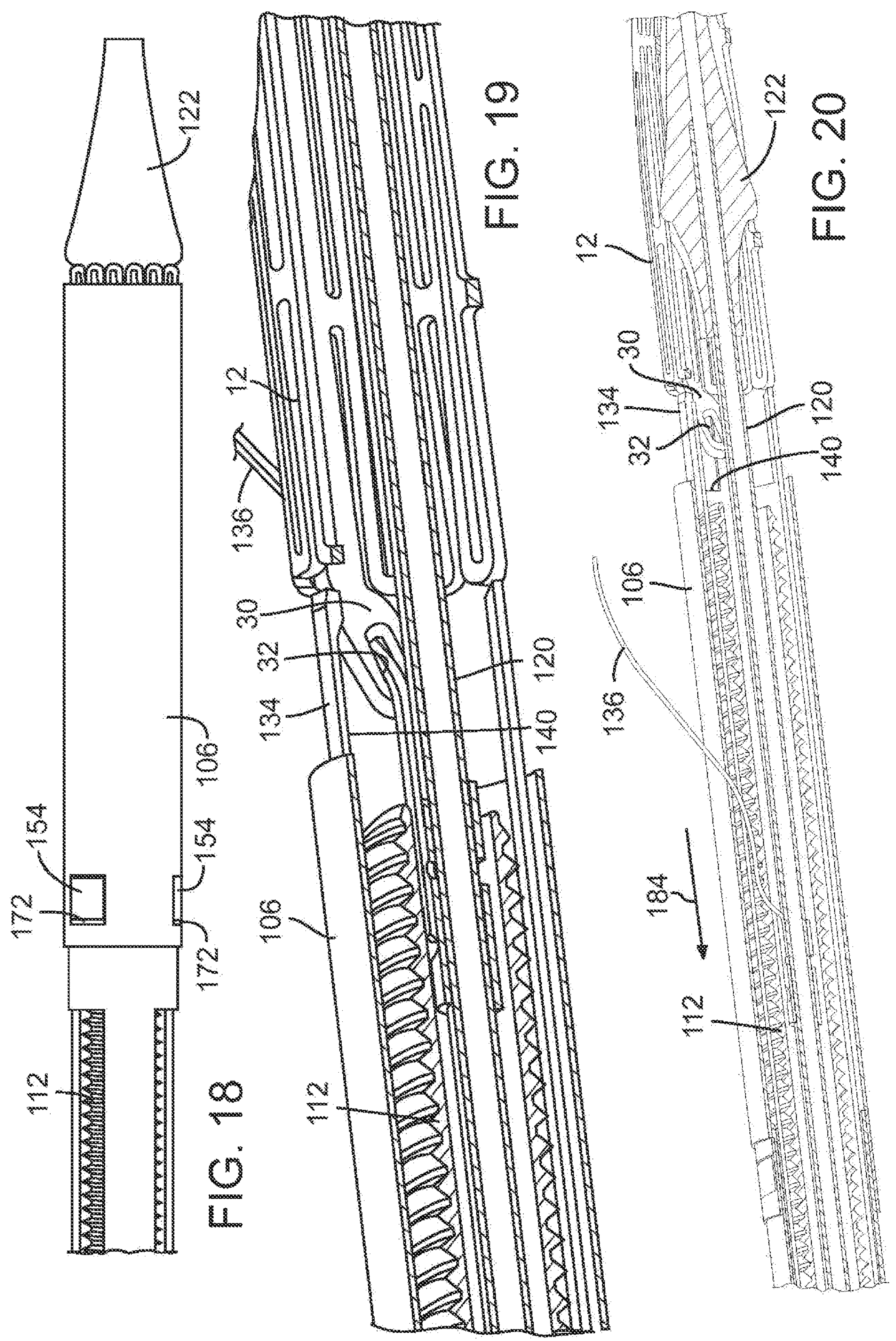
FIG. 18 is an enlarged side view of the distal end portion of the delivery apparatus of FIG. 8 showing the delivery sheath in a delivery position covering a prosthetic valve in a compressed state for delivery into a patient.
FIG. 19 is an enlarged cross-sectional view of a section of the distal end portion of the delivery apparatus of FIG. 8 showing the valve-retaining mechanism securing the stent of a prosthetic valve to the delivery apparatus.
FIG. 20 is an enlarged cross-sectional view similar to FIG. 19, showing the inner fork of the valve-retaining mechanism in a release position for releasing the prosthetic valve from the delivery apparatus.

The torque shaft 110 desirably is configured to be rotatable relative to the delivery sheath 106 to effect incremental and controlled advancement of the prosthetic valve 10 from the delivery sheath 106. To such ends, and according to one embodiment, the delivery apparatus 100 can include a sheath retaining ring in the form of a threaded nut 150 mounted on the external threads of the screw 112. As best shown in FIG. 16, the nut 150 includes internal threads 152 that engage the external threads of the screw and axially extending legs 154. Each leg 154 has a raised distal end portion that extends into and/or forms a snap fit connection with openings 172 in the proximal end of the sheath 106 (as best shown in FIG. 18) so as to secure the sheath 106 to the nut 150. As illustrated in FIGS. 17B and 18, the sheath 106 extends over the prosthetic valve 10 and retains the prosthetic valve in a radially compressed state until the sheath 106 is retracted by the user to deploy the prosthetic valve.

Figures 21, 22:
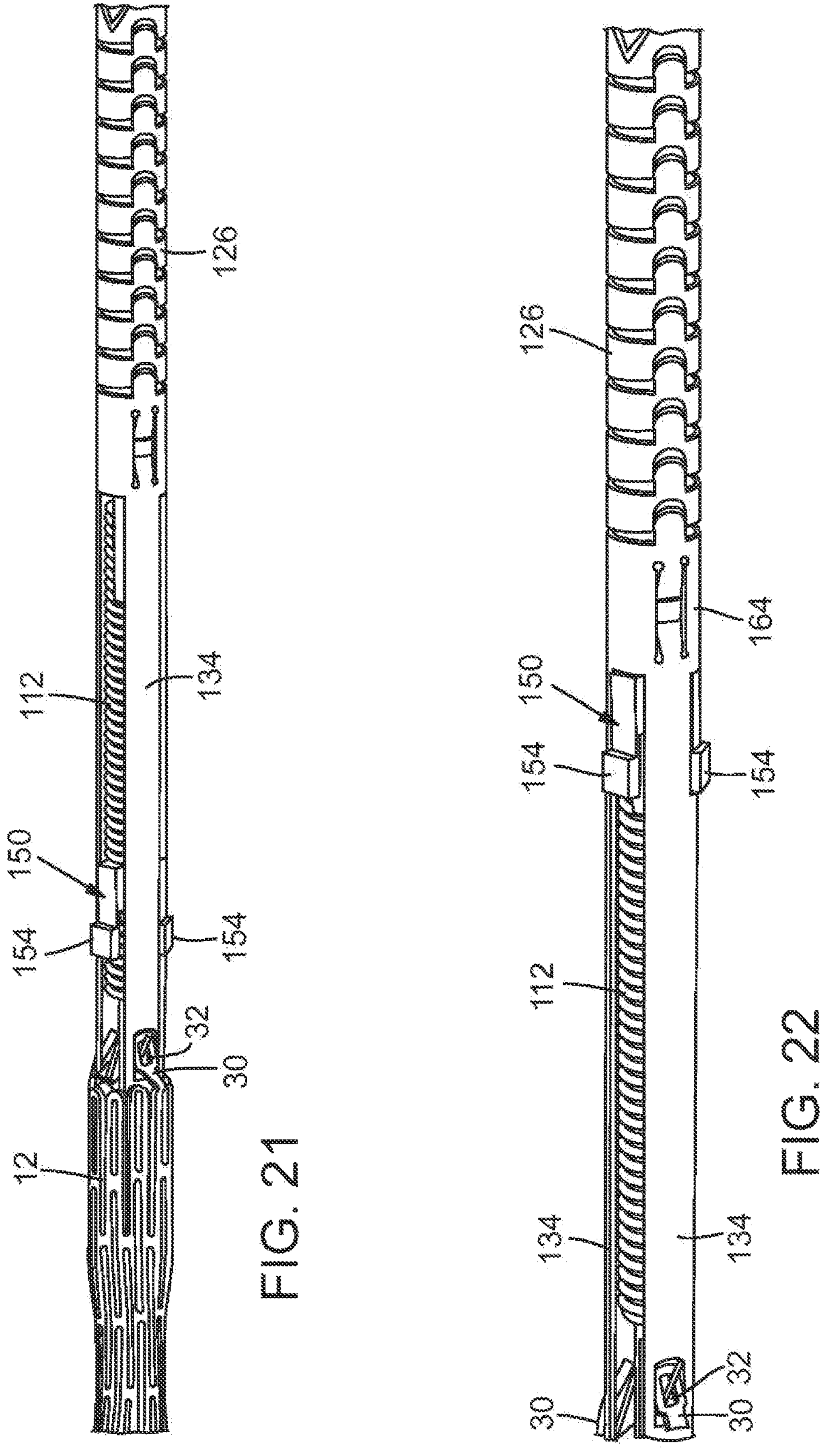
FIGS. 21 and 22 are enlarged side views of distal end portion of the delivery apparatus of FIG. 8, illustrating the operation of the torque shaft for deploying a prosthetic valve from a delivery sheath.

As best shown in FIGS. 21 and 22, the outer fork 130 of the valve-retaining mechanism comprises a plurality of prongs 134, each of which extends through a region defined between two adjacent legs 154 of the nut so as to prevent rotation of the nut relative to the screw 112 upon rotation of the screw. As such, rotation of the torque shaft 110 (and thus the screw 112) causes corresponding axial movement of the nut 150. The connection between the nut 150 and the sheath 106 is configured such that axially movement of the nut along the screw 112 (in the distal or proximal direction) causes the sheath 106 to move axially in the same direction relative to the screw and the valve-retaining mechanism. FIG. 21 shows the nut 150 in a distal position wherein the sheath 106 (not shown in FIG. 21) extends over and retains the prosthetic valve 10 in a compressed state for delivery. Movement of the nut 150 from the distal position (FIG. 21) to a proximal position (FIG. 22) causes the sheath 106 to move in the proximal direction, thereby deploying the prosthetic valve from the sheath 106. Rotation of the torque shaft 110 to effect axial movement of the sheath 106 can be accomplished with a motorized mechanism or by manually turning a crank or wheel (e.g., as described in U.S. Patent Application Publication No. 2012/0239142, which is incorporated by reference herein in its entirety).

FIG. 17 shows an enlarged view of the nose cone 122 secured to the distal end of the innermost shaft 120. The nose cone 122 in the illustrated embodiment includes a proximal end portion 174 that is sized to fit inside the distal end of the sheath 106. An intermediate section 176 of the nose cone is positioned immediately adjacent the end of the sheath in use and is formed with a plurality of longitudinal grooves or recessed portions 178. The diameter of the intermediate section 176 at its proximal end 180 desirably is slightly larger than the outer diameter of the sheath 106. The proximal end 180 can be held in close contact with the distal end of the sheath 106 to protect surrounding tissue from coming into contact with the metal edge of the sheath. The grooves 178 allow the intermediate section to be compressed radially as the delivery apparatus is advanced through an introducer sheath. This allows the nose cone 122 to be slightly oversized relative to the inner diameter of the introducer sheath. FIG. 17B shows a cross-section the nose cone 122 and the sheath 106 in a delivery position with the prosthetic valve retained in a compressed delivery state inside the sheath 106 (for purposes of illustration, only the stent 12 of the prosthetic valve is shown). As shown, the proximal end 180 of the intermediate section 176 can abut the distal end of the sheath 106 and a tapered proximal surface 182 of the nose cone can extend within a distal portion of the stent 12.

As noted above, the delivery apparatus 100 can include a valve-retaining mechanism 114 (FIG. 8B) for releasably retaining a stent 12 of a prosthetic valve. The valve-retaining mechanism 114 can include a first valve-securement component in the form of an outer fork 130 (as best shown in FIG. 12) (also referred to as an "outer trident" or "release trident"), and a second valve-securement component in the form of an inner fork 132 (as best shown in FIG. 17) (also referred to as an "inner trident" or "locking trident"). The outer fork 130 cooperates with the inner fork 132 to form a releasably connection with the retaining arms 30 of the stent 12.

The proximal end of the outer fork 130 is connected to the distal segment 126 of the outer shaft 104 and the distal end of the outer fork is releasably connected to the stent 12. In the illustrated embodiment, the outer fork 130 and the distal segment 126 can be integrally formed as a single component (e.g., the outer fork and the distal segment can be laser cut or otherwise machined from a single piece of metal tubing), although these components can be separately formed and subsequently connected to each other. The inner fork 132 can be mounted on the nose catheter shaft 120 (as best shown in FIG. 17). The inner fork 132 connects the stent to the distal end portion of the nose catheter shaft 120. The nose catheter shaft 120 can be moved axially relative to the outer shaft 104 to release the prosthetic valve from the valve-retaining mechanism, as further described below.

As best shown in FIG. 12, the outer fork 130 includes a plurality of angularly-spaced prongs 134 (three in the illustrated embodiment) corresponding to the retaining arms 30 of the stent 12, which prongs extend from the distal end of distal segment 126. The distal end portion of each prong 134 includes a respective opening 140. As best shown in FIG. 17, the inner fork 132 includes a plurality of angularly-spaced prongs 136 (three in the illustrated embodiment) corresponding to the retaining arms 30 of the stent 12, which prongs extend from a base portion 138 at the proximal end of the inner fork. The base portion 138 of the inner fork is fixedly secured to the nose catheter shaft 120 (e.g., with a suitable adhesive) to prevent axial and rotational movement of the inner fork relative to the nose catheter shaft 120.

Figure 30:
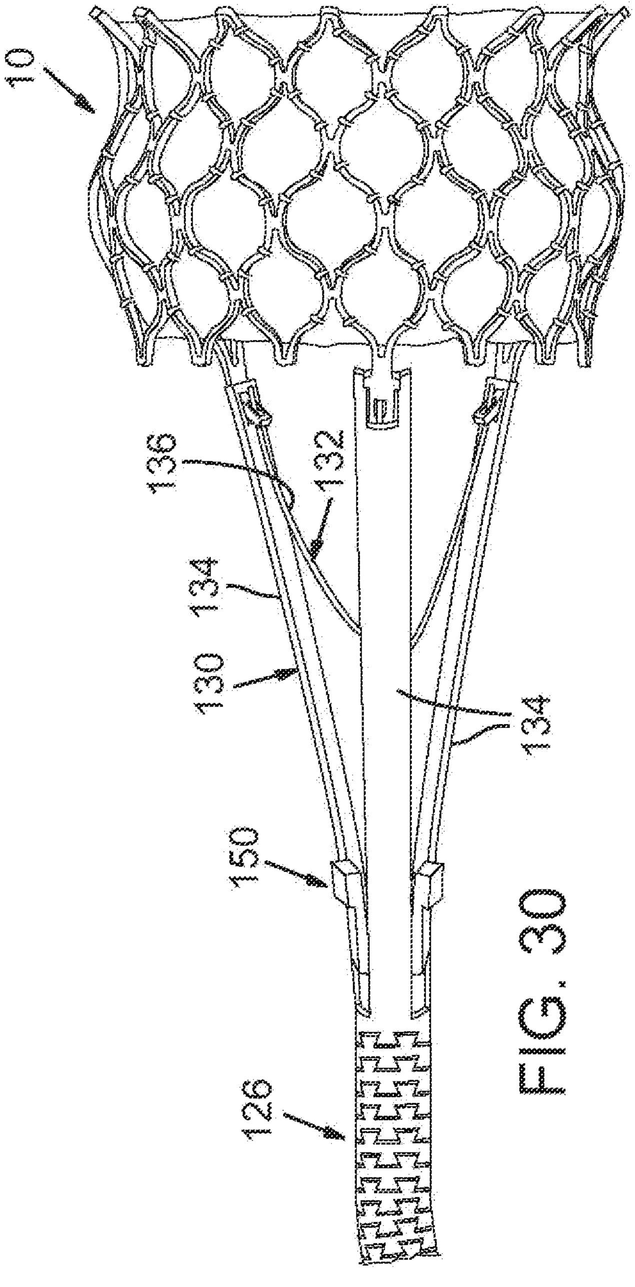
FIG. 30 is a perspective view of a prosthetic valve secured to the end of a delivery apparatus, according to one embodiment.

Each prong of the outer fork 130 cooperates with a corresponding prong 136 of the inner fork to form a releasable connection with a retaining arm 30 of the stent. In the illustrated embodiment, for example, the distal end portion of each prong 134 is formed with an opening 140. When the prosthetic valve is secured to the delivery apparatus (as best shown in FIG. 19), each retaining arm 30 of the stent 12 extends inwardly through an opening 140 of a prong 134 of the outer fork and a prong 136 of the inner fork is inserted through the opening 32 of the retaining arm 30 so as to retain the retaining arm 30 from backing out of the opening 140. FIG. 30 also shows the prosthetic valve 10 secured to the delivery apparatus by the inner and outer forks before the prosthetic valve is loaded into the sheath 106. The threaded nut 150 can be seen positioned between the prongs of the outer fork 130. The prosthetic valve 10 is ready to be compressed and loaded into the sheath 106 of a delivery apparatus. Retracting the inner prongs 136 proximally (in the direction of arrow 184 in FIG. 20) to remove the prongs from the openings 32 is effective to release the prosthetic valve 10 from the retaining mechanism. When the inner fork 132 is moved to a proximal position (FIG. 20), the retaining arms 30 of the stent can move radially outwardly from the openings 140 in the outer fork 130 under the resiliency of the stent. In this manner, the valve-retaining mechanism 114 forms a releasable connection with the prosthetic valve that is secure enough to retain the prosthetic valve relative to the delivery apparatus to allow the user to fine tune or adjust the position of the prosthetic valve after it is deployed from the delivery sheath. When the prosthetic valve is positioned at the desired implantation site, the connection between the prosthetic valve and the retaining mechanism can be released by retracting the nose catheter shaft 120 relative to the outer shaft 104 (which retracts the inner fork 132 relative to the outer fork 130).

Once the prosthetic valve 10 is loaded in the delivery sheath 106, the delivery apparatus 100 can be inserted into the patient's body for delivery of the prosthetic valve. In one approach, the prosthetic valve can be delivered in a retrograde procedure where delivery apparatus is inserted, for example, into a femoral artery and advanced through the patient's vasculature to the heart. Prior to insertion of the delivery apparatus, an introducer sheath can be inserted into the femoral artery followed by a guide wire, which is advanced through the patient's vasculature through the aorta and into the left ventricle. The delivery apparatus 100 can then be inserted through the introducer sheath and advanced over the guide wire until the distal end portion of the delivery apparatus containing the prosthetic valve 10 is advanced to a location adjacent to or within the native aortic valve.

Thereafter, the prosthetic valve 10 can be deployed from the delivery apparatus 100 by rotating the torque shaft 110 relative to the outer shaft 104. As described below, the proximal end of the torque shaft 110 can be operatively connected to a manually rotatable handle portion or a motorized mechanism that allows the surgeon to effect rotation of the torque shaft 110 relative to the outer shaft 104. Rotation of the torque shaft 110 and the screw 112 causes the nut 150 and the sheath 106 to move in the proximal direction toward the outer shaft (FIG. 22), which deploys the prosthetic valve from the sheath. Rotation of the torque shaft 110 causes the sheath to move relative to the prosthetic valve in a precise and controlled manner as the prosthetic valve advances from the open distal end of the delivery sheath and begins to expand. Hence, unlike known delivery apparatus, as the prosthetic valve begins to advance from the delivery sheath and expand, the prosthetic valve is held against uncontrolled movement from the sheath caused by the expansion force of the prosthetic valve against the distal end of the sheath. In addition, as the sheath 106 is retracted, the prosthetic valve 10 is retained in a stationary position relative to the ends of the inner shaft 120 and the outer shaft 104 by virtue of the valve-retaining mechanism 114. As such, the prosthetic valve 10 can be held stationary relative to the target location in the body as the sheath is retracted. Moreover, after the prosthetic valve is partially advanced from the sheath, it may be desirable to retract the prosthetic valve back into the sheath, for example, to reposition the prosthetic valve or to withdraw the prosthetic valve entirely from the body. The partially deployed prosthetic valve can be retracted back into the sheath by reversing the rotation of the torque shaft, which causes the sheath 106 to advance back over the prosthetic valve in the distal direction.

In known delivery devices, the surgeon must apply push-pull forces to the shaft and/or the sheath to unsheathe the prosthetic valve. It is therefore difficult to transmit forces to the distal end of the device without distorting the shaft (e.g., compressing or stretching the shaft axially), which in turn causes uncontrolled movement of the prosthetic valve during the unsheathing process. To mitigate this effect, the shaft and/or sheath can be made more rigid, which is undesirable because the device becomes harder to steer through the vasculature. In contrast, the manner of unsheathing the prosthetic valve described above eliminates the application of push-pull forces on the shaft, as required in known devices, so that relatively high and accurate forces can be applied to the distal end of the shaft without compromising the flexibility of the device. In certain embodiments, as much as about 90 N (about 20 lb) of force can be transmitted to the end of the torque shaft without adversely affecting the unsheathing process. In contrast, prior art devices utilizing push-pull mechanisms typically cannot exceed about 20 N (5 lb) of force during the unsheathing process.

After the prosthetic valve 10 is advanced from the delivery sheath and expands to its functional size (the expanded prosthetic valve 10 secured to the delivery apparatus is depicted in FIG. 30), the prosthetic valve remains connected to the delivery apparatus via the retaining mechanism 114. Consequently, after the prosthetic valve is advanced from the delivery sheath, the surgeon can reposition the prosthetic valve relative to the desired implantation position in the native valve such as by moving the delivery apparatus in the proximal and distal directions or side to side, or rotating the delivery apparatus, which causes corresponding movement of the prosthetic valve. The retaining mechanism 114 desirably provides a connection between the prosthetic valve and the delivery apparatus that is secure and rigid enough to retain the position of the prosthetic valve relative to the delivery apparatus against the flow of the blood as the position of the prosthetic valve is adjusted relative to the desired implantation position in the native valve. Once the surgeon positions the prosthetic valve at the desired implantation position in the native valve, the connection between the prosthetic valve and the delivery apparatus can be released by retracting the innermost shaft 120 in the proximal direction relative to the outer shaft 104, which is effective to retract the inner fork 132 to withdraw its prongs 136 from the openings 32 in the retaining arms 30 of the prosthetic valve (FIG. 20). Slightly retracting of the outer shaft 104 allows the outer fork 130 to back off the retaining arms 30 of the prosthetic valve, which slide outwardly through openings 140 in the outer fork to completely disconnect the prosthetic valve from the retaining mechanism 114. Thereafter, the delivery apparatus can be withdrawn from the body, leaving the prosthetic aortic valve 10 implanted within the native valve (such as shown in FIGS. 5A and 5B).

The delivery apparatus 100 has at its distal end a semi-rigid segment comprised of relatively rigid components used to transform rotation of the torque shaft into axial movement of the sheath. In particular, this semi-rigid segment in the illustrated embodiment is comprised of the prosthetic valve and the screw 112. An advantage of the delivery apparatus 100 is that the overall length of the semi-rigid segment is minimized because the nut 150 is used rather than internal threads on the outer shaft to affect translation of the sheath. The reduced length of the semi-rigid segment increases the overall flexibility along the distal end portion of the delivery catheter. Moreover, the length and location of the semi-rigid segment remains constant because the torque shaft does not translate axially relative to the outer shaft. As such, the curved shape of the delivery catheter can be maintained during valve deployment, which improves the stability of the deployment. A further benefit of the delivery apparatus 100 is that the ring 128 prevents the transfer of axial loads (compression and tension) to the section of the torque shaft 110 that is distal to the ring.

In an alternative embodiment, the delivery apparatus can be adapted to deliver a balloon-expandable prosthetic valve. As described above, the valve retaining mechanism 114 can be used to secure the prosthetic valve to the end of the delivery apparatus. Since the stent of the prosthetic valve is not self-expanding, the sheath 106 can be optional. The retaining mechanism 114 enhances the pushability of the delivery apparatus and prosthetic valve assembly through an introducer sheath.

FIGS. 23-26 illustrate the proximal end portion of the delivery apparatus 100, according to one embodiment. The delivery apparatus 100 can comprise a handle 202 that is configured to be releasably connectable to the proximal end portion of a catheter assembly 204 comprising catheters 102, 108, 118. It may be desirable to disconnect the handle 202 from the catheter assembly 204 for various reasons. For example, disconnecting the handle can allow another device to be slid over the catheter assembly, such as a valve-retrieval device or a device to assist in steering the catheter assembly. It should be noted that any of the features of the handle 202 and the catheter assembly 204 can be implemented in any of the embodiments of the delivery apparatuses disclosed herein.

Figures 23, 24:
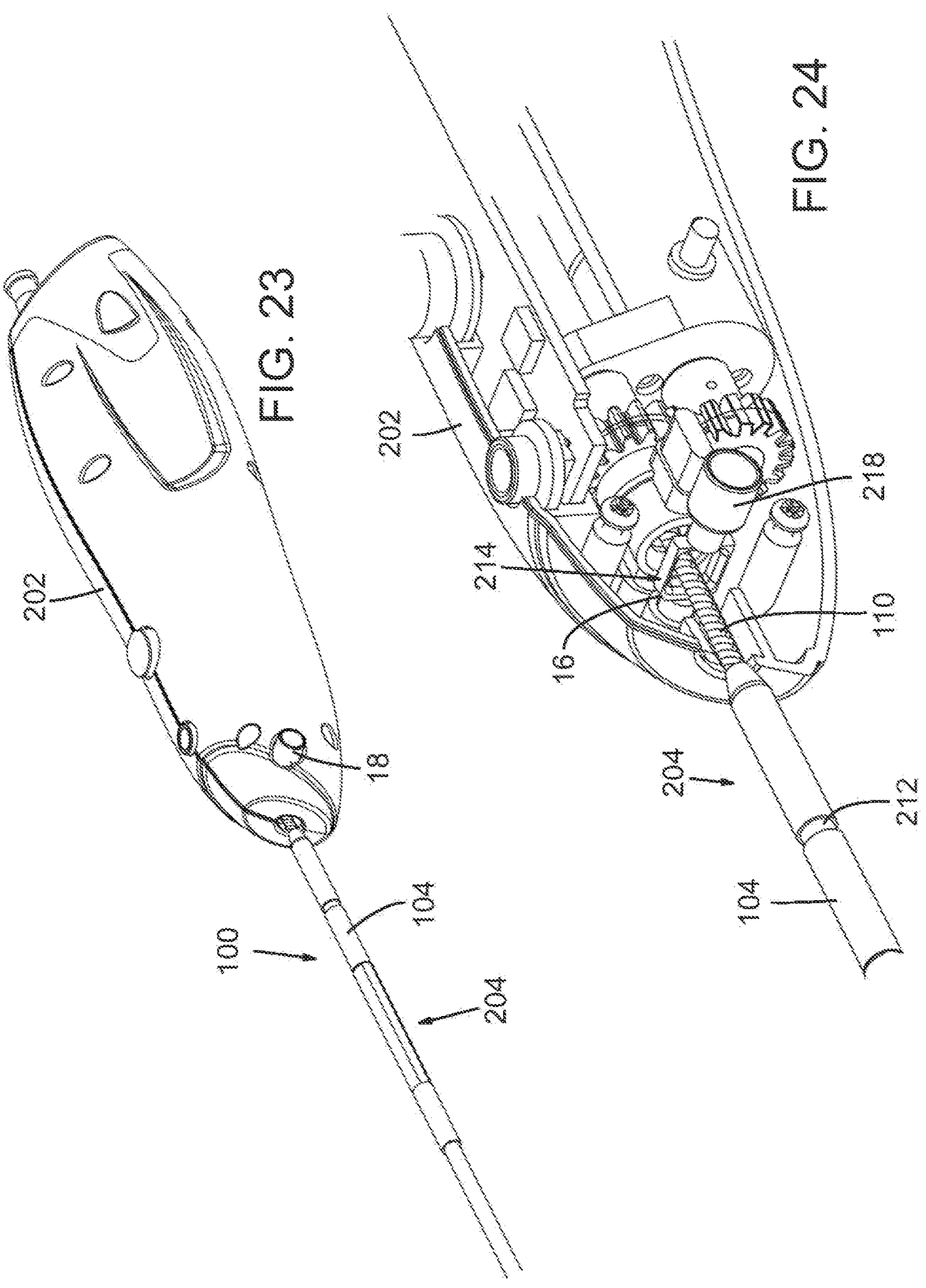
FIGS. 23-26 are various views of an embodiment of a motorized delivery apparatus that can be used to operate the torque shaft of the delivery apparatus shown in FIG. 8.
Figures 25, 26, 27:
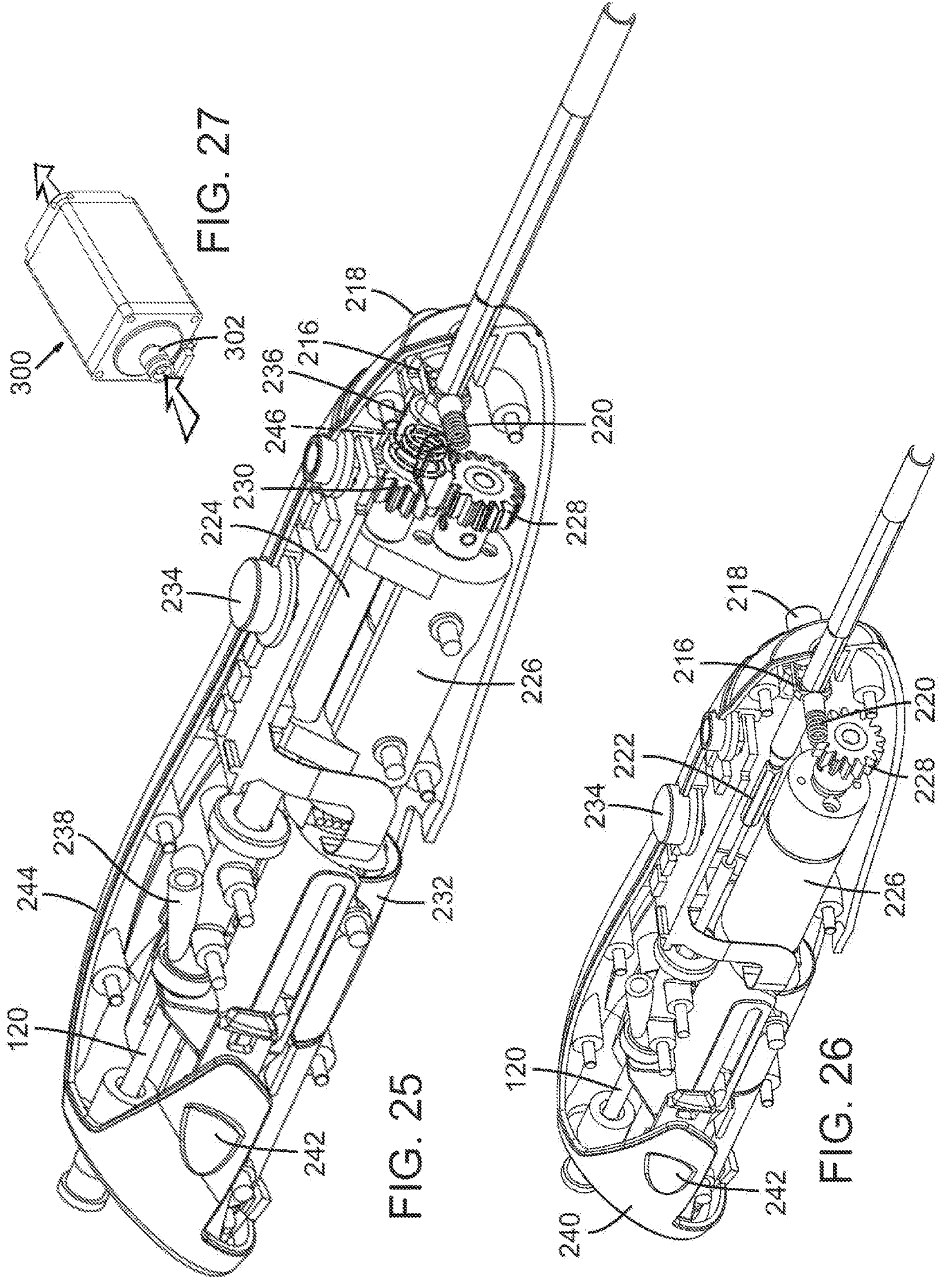
FIG. 27 is a perspective view of an alternative motor that can be used to operate the torque shaft of the delivery apparatus shown in FIG. 8.

FIGS. 23 and 24 show the proximal end portion of the catheter assembly 204 partially inserted into a distal opening of the handle 202. The proximal end portion of the main shaft 104 is formed with an annular groove 212 (as best shown in FIG. 24) that cooperates with a holding mechanism, or latch mechanism, 214 inside the handle. When the proximal end portion of the catheter assembly is fully inserted into the handle, as shown in FIGS. 25 and 26, an engaging portion 216 of the holding mechanism 214 extends at least partially into the groove 212. One side of the holding mechanism 214 is connected to a button 218 that extends through the housing of the handle. The opposite side of the holding mechanism 214 is contacted by a spring 220 that biases the holding mechanism to a position engaging the main shaft 104 at the groove 212. The engagement of the holding mechanism 214 within the groove 212 prevents axial separation of the catheter assembly from the handle. The catheter assembly can be released from the handle by depressing button 218, which moves the holding mechanism 214 from locking engagement with the main shaft. Furthermore, the main shaft 104 can be formed with a flat surface portion within the groove 212. The flat surface portion is positioned against a corresponding flat surface portion of the engaging portion 216. This engagement holds the main shaft 104 stationary relative to the torque shaft 110 as the torque shaft is rotated during valve deployment.

The proximal end portion of the torque shaft 110 can have a driven nut 222 (FIG. 26) that is slidably received in a drive cylinder 224 (FIG. 25) mounted inside the handle. The nut 222 can be secured to the proximal end of the torque shaft 100 by securing the nut 222 over a coupling member 170 (FIG. 15). FIG. 26 is a perspective view of the inside of the handle 202 with the drive cylinder and other components removed to show the driven nut and other components positioned within the drive cylinder. The cylinder 224 has a through opening (or lumen) extending the length of the cylinder that is shaped to correspond to the flats of the nut 222 such that rotation of the drive cylinder is effective to rotate the nut 222 and the torque shaft 110. The drive cylinder can have an enlarged distal end portion 236 that can house one or more seals (e.g., O-rings 246) that form a seal with the outer surface of the main shaft 104 (FIG. 25). The handle can also house a fitting 238 that has a flush port in communication with the lumen of the torque shaft and/or the lumen of the main shaft.

The drive cylinder 224 is operatively connected to an electric motor 226 through gears 228 and 230. The handle can also house a battery compartment 232 that contains batteries for powering the motor 226. Rotation of the motor in one direction causes the torque shaft 110 to rotate, which in turn causes the sheath 106 to retract and uncover a prosthetic valve at the distal end of the catheter assembly. Rotation of the motor in the opposite direction causes the torque shaft to rotate in an opposite direction, which causes the sheath to move back over the prosthetic valve. An operator button 234 on the handle allows a user to activate the motor, which can be rotated in either direction to un-sheath a prosthetic valve or retrieve an expanded or partially expanded prosthetic valve.

As described above, the distal end portion of the nose catheter shaft 120 can be secured to an inner fork 132 that is moved relative to an outer fork 130 to release a prosthetic valve secured to the end of the delivery apparatus. Movement of the shaft 120 relative to the main shaft 104 (which secures the outer fork 130) can be effected by a proximal end portion 240 of the handle that is slidable relative to the main housing 244. The end portion 240 is operatively connected to the shaft 120 such that movement of the end portion 240 is effective to translate the shaft 120 axially relative to the main shaft 104 (causing a prosthetic valve to be released from the inner and outer forks). The end portion 240 can have flexible side panels 242 on opposite sides of the handle that are normally biased outwardly in a locked position to retain the end portion relative to the main housing 244. During deployment of the prosthetic valve, the user can depress the side panels 242, which disengage from corresponding features in the housing and allow the end portion 240 to be pulled proximally relative to the main housing, which causes corresponding axial movement of the shaft 120 relative to the main shaft. Proximal movement of the shaft 120 causes the prongs 136 of the inner fork 132 to disengage from the apertures 32 in the stent 12, which in turn allows the retaining arms 30 of the stent to deflect radially outwardly from the openings 140 in the prongs 134 of the outer fork 130, thereby releasing the prosthetic valve.

FIG. 27 shows an alternative embodiment of a motor, indicated at 300, that can be used to drive a torque shaft (e.g., torque shaft 110). In this embodiment, a catheter assembly can be connected directly to one end of a shaft 302 of the motor, without gearing. The shaft 302 includes a lumen that allows for passage of an innermost shaft (e.g., shaft 120) of the catheter assembly, a guide wire, and/or fluids for flushing the lumens of the catheter assembly.

Alternatively, the power source for rotating the torque shaft 110 can be a hydraulic power source (e.g., hydraulic pump) or pneumatic (air-operated) power source that is configured to rotate the torque shaft. In another embodiment, the handle can have a manually movable lever or wheel that is operable to rotate the torque shaft 110.

In another embodiment, a power source (e.g., an electric, hydraulic, or pneumatic power source) can be operatively connected to a shaft, which is turn is connected to a prosthetic valve 10. The power source is configured to reciprocate the shaft longitudinally in the distal direction relative to a valve sheath in a precise and controlled manner in order to advance the prosthetic valve from the sheath. Alternatively, the power source can be operatively connected to the sheath in order to reciprocate the sheath longitudinally in the proximal direction relative to the prosthetic valve to deploy the prosthetic valve from the sheath.

Figures 31, 32:
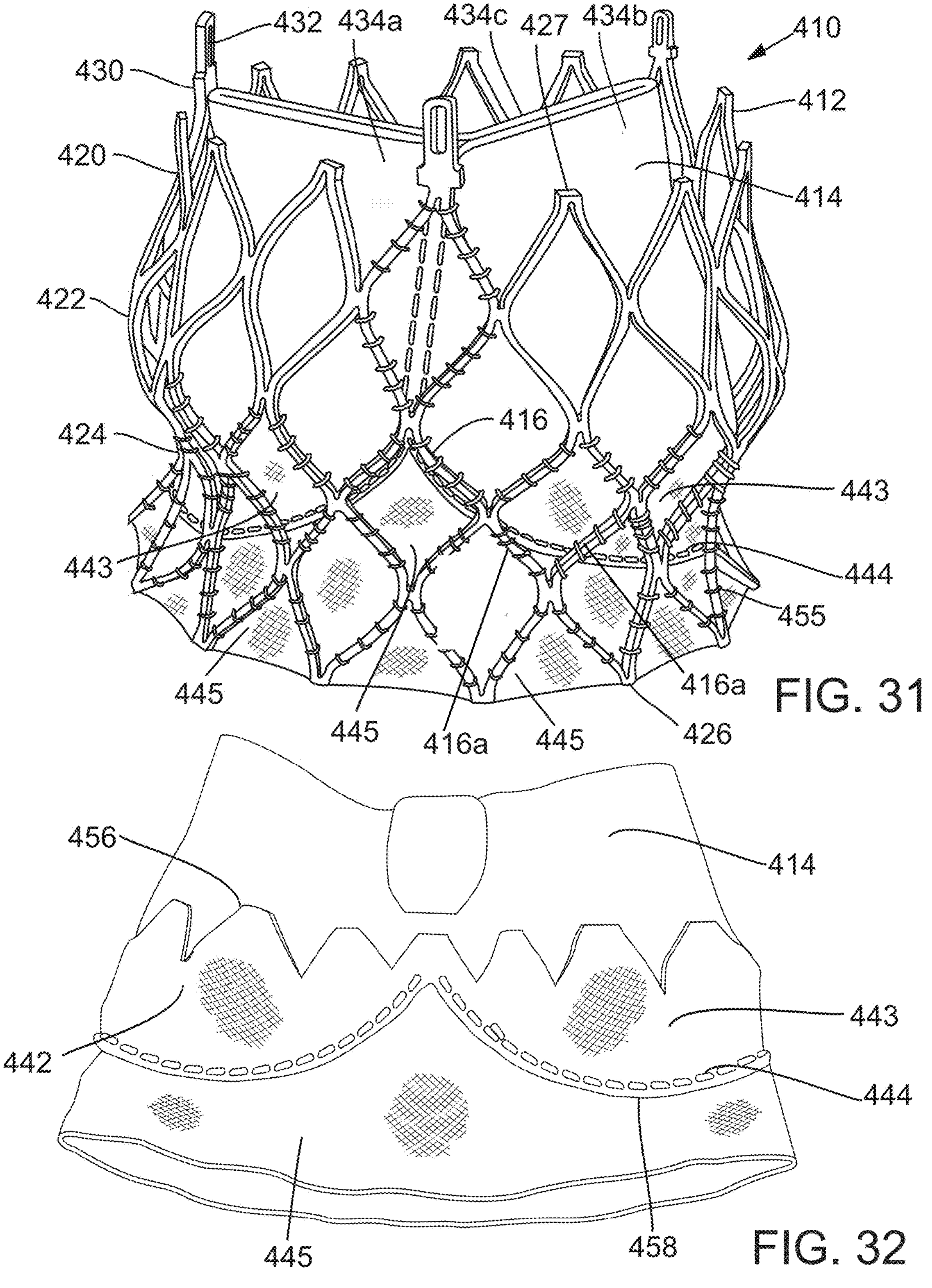
FIG. 31 is a perspective view of a prosthetic valve that can be used to replace the native aortic valve of the heart, according to another embodiment.
FIG. 32 is a perspective view of the leaflet structure, also showing the skirt including an upper and lower skirt, of the prosthetic valve of FIG. 31 shown prior to being secured to the support frame.

Referring to FIG. 31, there is shown a prosthetic aortic heart valve 410, according to another embodiment. Similar to the prosthetic valve 10, the prosthetic valve 410 includes an expandable frame member, or stent, 412 that supports an expandable valve member, which in the illustrated embodiment comprises a flexible leaflet section 414. Also, the prosthetic valve 410 is radially compressible to a compressed state for delivery through the body to a deployment site and expandable to its functional size shown in FIG. 31 at the deployment site. In certain embodiments, the prosthetic valve 410 is self-expanding; that is, the prosthetic valve can radially expand to its functional size when advanced from the distal end of a delivery sheath. In other embodiments, the prosthetic valve can be a balloon-expandable prosthetic valve that can be adapted to be mounted in a compressed state on the balloon of a delivery catheter. The prosthetic valve can be expanded to its functional size at a deployment site by inflating the balloon, as known in the art. Apparatuses particularly suited for percutaneous delivery and implantation of the prosthetic valve 10 (such as those described herein) are also suitable for percutaneous delivery and implantation of the prosthetic valve 410. The illustrated prosthetic valve 410 is adapted to be deployed in the native aortic annulus, although it also can be used to replace the other native valves of the heart (the mitral, tricuspid and pulmonary valves). Moreover, the prosthetic valve 410 can be adapted to replace other valves within the body, such venous valves.

The frame member 412 of the prosthetic valve 410 can have the same overall shape and construction as the frame member 12 of the prosthetic valve 10. Thus, similar to the frame member 12, the frame member 412 can be formed from a plurality of longitudinally extending, generally sinusoidal shaped frame members, or struts, 416. Referring to FIG. 31, the stent 412 has an inflow end 426 and an outflow end 427, and the mesh structure formed by the struts 416 comprises a generally cylindrical "upper" or outflow end portion 420, an outwardly bowed or distended intermediate section 422, and an inwardly bowed "lower" or inflow end portion 424. Further, the stent 412 can have a plurality of angularly spaced retaining arms, or projections, in the form of posts 430 (three in the illustrated embodiment) that extend from upper portion of the stent 412. Each retaining arm 430 has a respective aperture 432 that is sized to receive prongs of a valve-retaining mechanism that can be used to form a releasable connection between the prosthetic valve and a delivery apparatus (described above). In alternative embodiments, the retaining arms 430 need not be provided if a valve-retaining mechanism is not used. In further embodiments, the retaining arms 430 can extend from the lower portion of the stent 424, for example, for applications involving antegrade implantation of the valve (e.g., the delivery apparatus is inserted through a surgical opening in the wall of the left ventricle of the heart in a transventricular approach, such as an opening made at the bare spot on the lower anterior ventricle wall).

The leaflet assembly 414 of the prosthetic aortic heart valve 410 is similar to the leaflet assembly 14 of the prosthetic aortic heart valve 10, although there are several differences, described below. For example, with reference to FIGS. 32 and 33, the leaflet assembly 414 comprises three leaflets 434_a_, 434_b_, 434_c_ made of a flexible material. Each leaflet has an inflow end portion 460 and an outflow end portion 462. The leaflets can comprise any suitable biological material (e.g., pericardial tissue, such as bovine or equine pericardium), bio-compatible synthetic materials, or other such materials, such as those described in U.S. Pat. No. 6,730,118, which is incorporated herein by reference. The leaflet assembly 414 can include an annular reinforcing skirt assembly 442 that is secured to the inflow end portions of the leaflets 434_a_, 434_b_, 434_c_ at a suture line 444 adjacent the inflow end of the prosthetic valve. The inflow end portion of the leaflet assembly 414 can be secured to the stent 412 by suturing the skirt assembly 442 to the struts 416 of the lower section 424 of the stent (best shown in FIG. 31).

Figure 33:
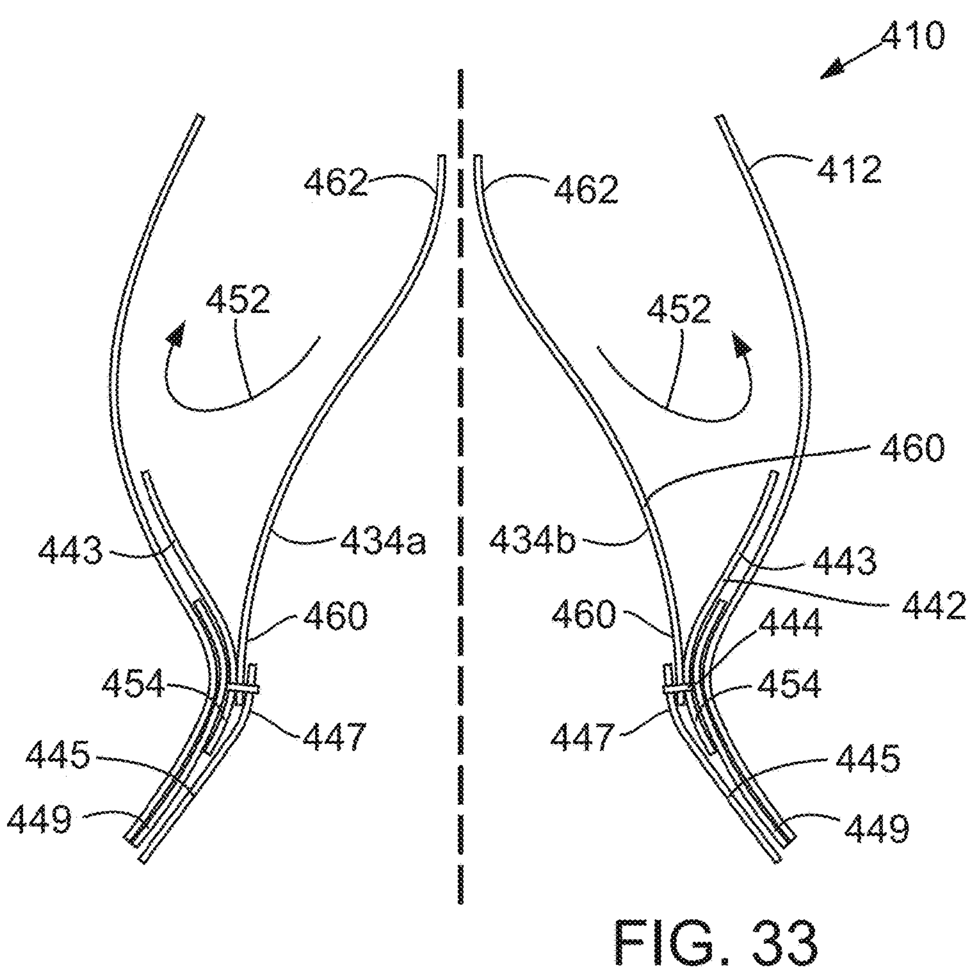
FIG. 33 is a cross-sectional view of the prosthetic valve of FIG. 31 illustrating the configuration of the valve frame, the leaflets, the upper skirt, the lower skirt, and the sealing skirt, in one embodiment.

With reference to FIG. 33, the skirt assembly 442 can include an upper skirt 443 and a lower skirt 445. The inflow end portions 460 of the leaflets 434_a_, 434_b_, and 434_c_ can be positioned between an upper portion 447 of the lower skirt 445 and a lower portion 454 of the upper skirt 443, with the upper skirt desirably having an outward placement compared to the lower skirt. The upper skirt 443, the inflow end portions 460 of the leaflets 434_a_, 434_b_, 434_c_, and the lower skirt 445 can be secured by sutures along a scalloped or undulating suture line 444 adjacent the inflow end of the prosthetic valve (FIG. 31). As best shown in FIG. 31, the undulating suture line 444 transects struts 416_a_ that form a first, inflow row of cells of the frame. The inflow end portion of the leaflet assembly 414 can be secured to the stent 412 by suturing the upper skirt 443, the lower skirt 445, or both the upper skirt 443 and the lower skirt 445 to the struts 416 of the lower section 424 of the stent via sutures 455 (best shown in FIG. 31). The skirt assembly 442 (including the upper skirt 443 and the lower skirt 445), desirably can be made of a bio-compatible synthetic material, such as polytetrafluoroethylene (PTFE), or a woven fabric material, such as woven polyester (e.g., polyethylene terephthalate) (PET), DACRON®). The upper skirt 443 and the lower skirt 445 can be made of the same, or different, material.

As best shown in FIG. 32, the outflow end portion of upper skirt 443 can be shaped to substantially align with the undulating or zigzag shape formed by the struts 416 of the lower section 424 of the stent, e.g., for ease of securing the upper skirt to the struts of the stent by suture. For example, the upper skirt 443 can include an upper edge 456 shaped to correspond to the shape of the second lowermost row of cells of the frame member 412. The inflow end portion of upper skirt 443 can have an undulating lower edge 458 that substantially aligns with the undulating suture line 444 and the scalloped or undulating shape of the inflow portions of the leaflets 443_a_, 443_b_, and 443_c_. The outflow end portion of the lower skirt 445 can be shaped to have an undulating shape that substantially corresponds with the undulating suture line 444. The inflow end portion 454 of the upper skirt 443 and the outflow end portion 447 of the lower skirt 445 overlap each other on opposite sides of the leaflet inflow end portions at least enough to secure the upper skirt and lower skirt by sutures along the suture line 444. The inflow end portion of the lower skirt 445 typically extends to the inflow end 426 of the stent, although other configurations are possible. For example, the inflow end portion of the lower skirt 445 can be shaped to include a lower edge shaped to correspond to the shape of a lowermost row of cells of the frame.

The outflow end portion of the leaflet assembly 414 can be secured to the upper portion of the stent 412 at three angularly spaced commissure attachments of the leaflets 434*a*, 434*b*, 434*c*, in a manner similar to the configuration used to secure the outflow end portion of the leaflet assembly 14 to the upper portion of the stent 12 at three angularly spaced commissure attachments of the leaflets 34*a*, 34*b*, 34*c* (as best shown in FIG. 2).

FIG. 33 shows the operation of the prosthetic valve 410. During diastole, the leaflets 434*a*, 434*b*, 434*c* collapse to effectively close the prosthetic valve. As shown, the curved shape of the intermediate section 422 of the stent 412 defines a space between the intermediate section and the leaflets that mimics the sinuses of Valsalva. Thus, when the leaflets close, backflow entering the "sinuses" creates a turbulent flow of blood along the upper surfaces of the leaflets, as indicated by arrows 452. This turbulence assists in washing the leaflets and the skirt assembly 442 to minimize clot formation.

Figures 35, 36, 37:
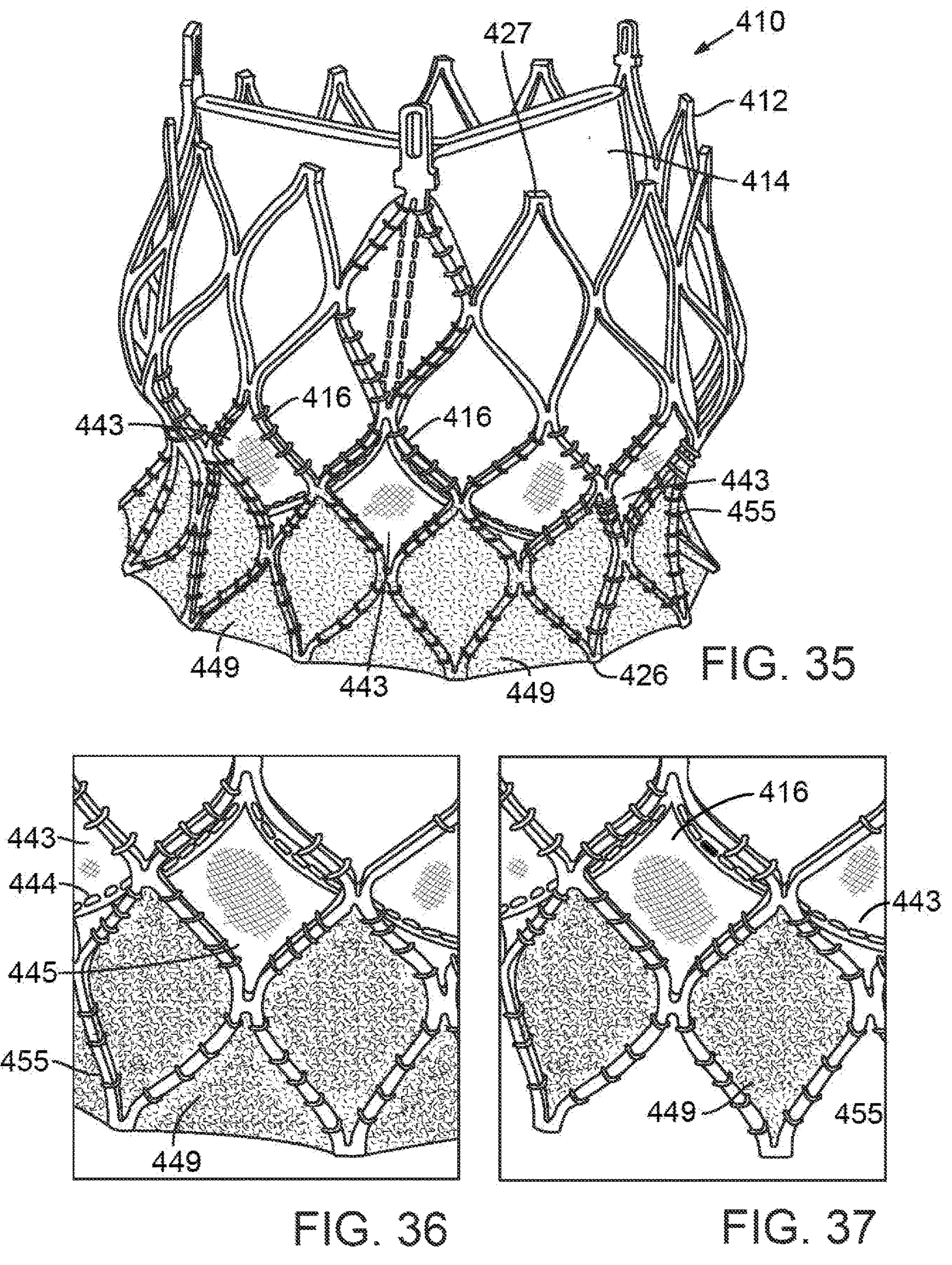
FIG. 35 is a perspective view of a prosthetic valve including a sealing skirt that can be used to replace the native aortic valve of the heart, according to one embodiment.
FIG. 36 is a perspective view of a portion of the prosthetic valve of FIG. 35 illustrating the sealing skirt and its connection to the support frame of the prosthetic valve, in one embodiment.
FIG. 37 is a perspective view similar to FIG. 36 illustrating a modification of the sealing skirt.

Referring to FIGS. 33 and 35, the prosthetic valve 410 can further include a sealing skirt 449 positioned at the lower section 424 of the stent. The sealing skirt 449 provides an additional barrier against paravalvular leakage following implantation of the stent in a subject by providing material at the inflow end portion of the stent that protrudes outwardly through the openings of the cells of the frame and contacts surrounding tissue of the native annulus, thereby minimizing or reducing paravalvular leakage. The sealing skirt is desirably supported by the upper skirt 443 and the lower skirt 445, which prevent the sealing skirt 449 from contacting the leaflets 434*a*, 434*b*, and 434*c* of the leaflet assembly 414. The upper skirt 443 and the lower skirt 445 additionally provide support to ensure that the material of the sealing skirt 449 extends outwardly between cells formed by the struts 416 of the stent 412 to seal against the surrounding annulus. As shown in FIGS. 33 and 35, the prosthetic valve 410 in these figures includes a first skirt (skirt 445), a second skirt (skirt 449), and a third skirt (skirt 443). As best shown in FIG. 31, the first skirt 445 covers cells of a first, inflow (lowermost) row of cells and a second row of cells downstream of the first row of cells. As best shown in FIG. 33, the first skirt 445 extends from the inflow end 426 of the frame 412 and overlaps the second skirt 449 along an inflow end portion of the frame.

Figure 34:
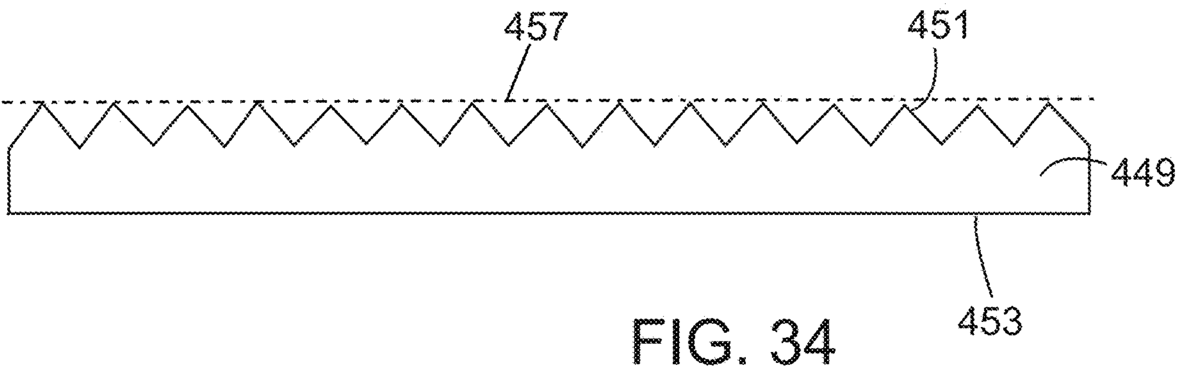
FIG. 34 is a diagram of the sealing skirt before attachment to the valve frame, in one embodiment.
Figure 38:
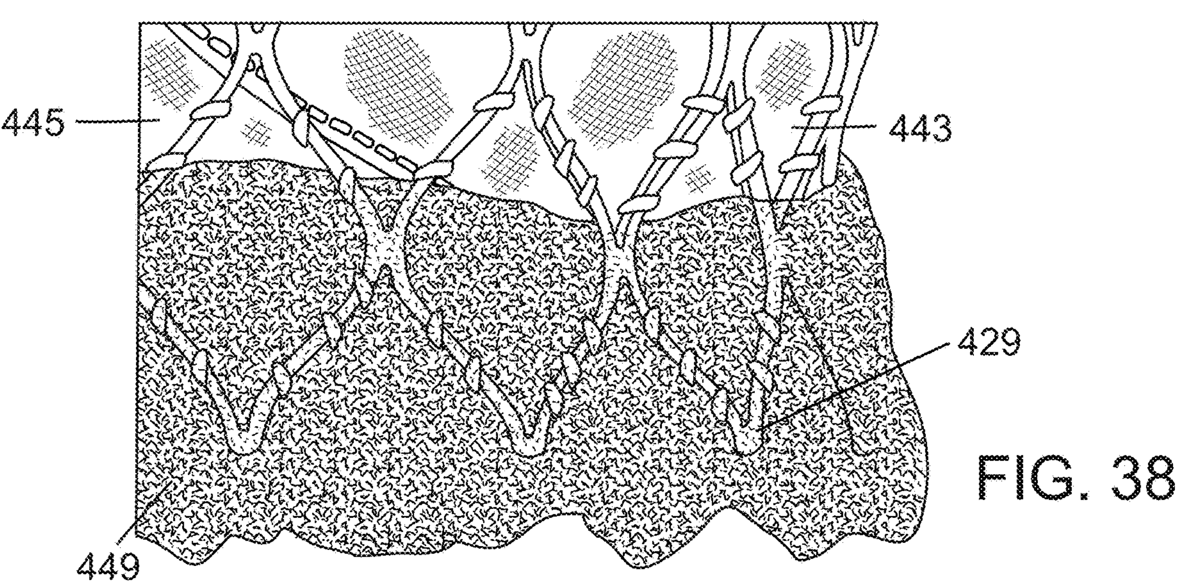
FIG. 38 is a perspective view similar to FIG. 36 illustrating a modification of the sealing skirt.

FIG. 34 depicts an embodiment of the sealing skirt 449 prior to attachment to the stent. The outflow end portion 451 of the sealing skirt 449 can have an undulating or zigzag shape that has an upper edge shaped to correspond to the shape of the upper boundary of a lower most row of cells of the frame formed by the struts 416 of the stent 412. In alternative embodiments, the outflow end portion 451 of the sealing (second) skirt 449 can have a substantially straight edge 457 that does not align with the undulating or zigzag shape formed by the struts 416 of the stent 412; instead the outflow end portion 451 of the sealing (second) skirt 449 can transect the lower most row of cells of the frame formed by the struts 416 of the stent 412 (see, e.g., FIG. 38). As shown in FIG. 34, the inflow end portion 453 of the second skirt 449 can have a straight lower edge. The inflow end portion 453 of the sealing skirt 449 typically extends to the inflow end 426 of the stent (see, e.g., FIGS. 35 and 36), although other configurations are possible. For example, the sealing skirt 449 can have an upper edge and a lower edge shaped to correspond to the shape of a lower most row of cells formed by the struts 416 of the inflow end 426 of the stent such that the sealing skirt 449 only occludes the openings in the lowermost row of cells (see, e.g., FIG. 37). In additional embodiments, the inflow end portion of the sealing (second) skirt 449 can be constructed to extend beyond the inflow end 426 of the stent (see, e.g., FIG. 38, which shows the inflow end portion of skirt 449 extending beyond apices 429 at the inflow end 426 of the stent). In several embodiments, the inflow end portion 453 of the sealing skirt 449 can be shaped to substantially align with the inflow end portion of the lower skirt 445.

Referring to FIGS. 35-39, the sealing skirt 449 can be secured to the struts 416 of the lower portion of the stent 412 with sutures 455. The sutures 455 can secure the sealing skirt 449 to the struts 416 of the lower portion of the stent 412, and optionally can also secure the upper skirt 443 and/or the lower skirt 445 to the struts 416 of the lower portion of the stent 412. The sealing skirt 449 desirably is made of a bio-compatible synthetic material, such as polytetrafluoroethylene (PTFE), or a woven fabric material, such as woven polyester (e.g., polyethylene terephthalate) (PET), DACRON®). In several embodiments, the sealing skirt comprises a plush or pile material, such as a loop yarn, which functions as a filler material in that fibers of the sealing skirt can extend outwardly through openings in the frame and fill spaces between the frame and the native annulus. The plush or pile material is also compressible, thus minimizing the crimp profile of the sealing skirt 449. In some embodiments, the sealing skirt can be made of a PET loop yarn or polyester 70/20 textured yarn. In additional embodiments, the sealing skit can be made of polyester multifilament partially oriented yarn (poy); a polyester 2-ply multifilament yarn; a polyester film; a knitted polyester; a woven polyester; and/or a felted polyester. Such materials are available commercially, for example, from Biomedical Structures (Warwick, RI) and ATEX Technologies (Pinebluff, NC).

Figure 39:
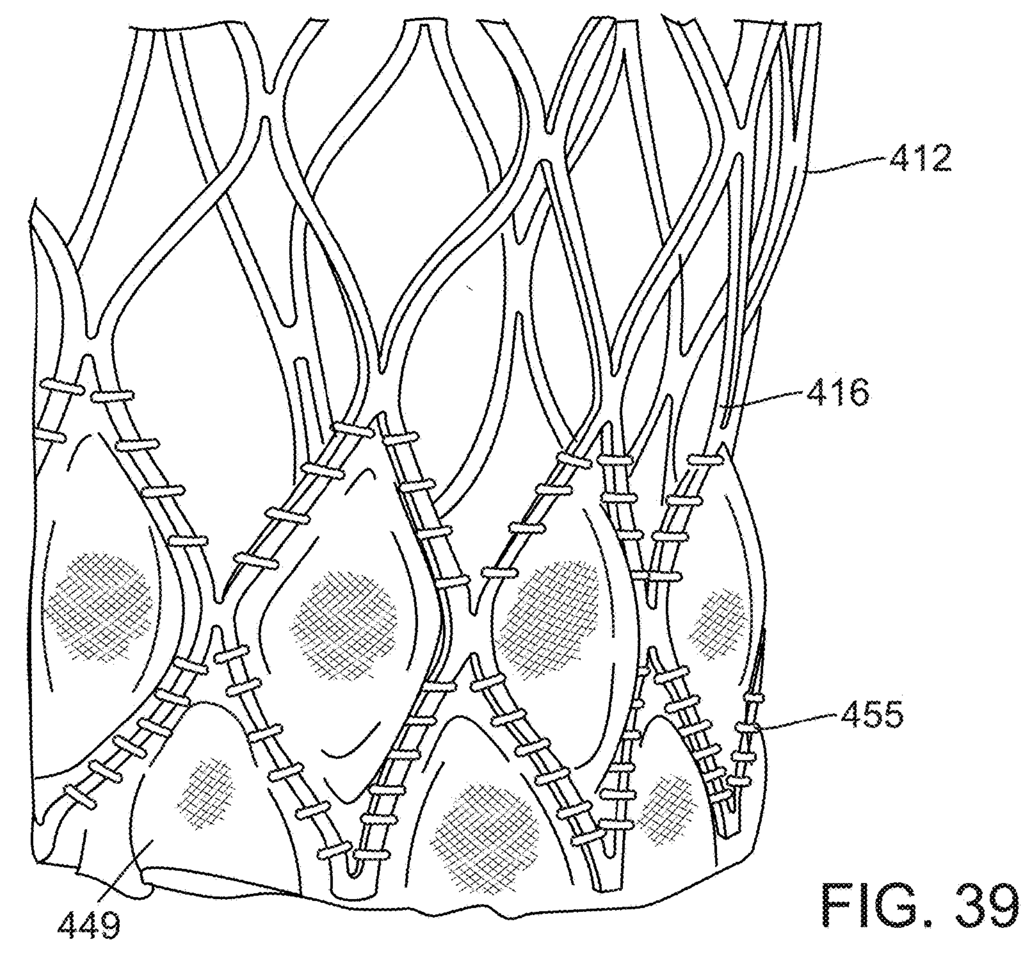
FIG. 39 is a perspective view of a portion of the prosthetic valve of FIG. 35 illustrating another configuration of the sealing skirt.

With reference to FIG. 39, the illustrated embodiment of the sealing skirt 449 can be made of a relatively less bulky, non-plush or non-pile material (e.g., woven PET fabric) and secured (e.g., with sutures 455) to the frame member 412 such that portions of the sealing skirt protrude radially outwardly through the cells of the frame member 412 to seal against the surrounding annulus. In such embodiments, the sealing skirt can be secured by sutures 455 such that slack material of sealing skirt 449 bulges or protrudes through the lowermost cells formed by the struts 416 of the frame member 412. The lower skirt 445 supports the sealing skirt 449 (and can be secured to the frame member 412 with the same sutures 455 as used to secure the sealing skirt 449) to prevent the slack material of the sealing skirt from protruding inwardly towards the longitudinal axis of the valve 410 and contacting the leaflets. In such embodiments, the length of the sealing skirt 449 is typically longer than that of the inner circumference of the lower portion of the frame member 412. FIG. 39 provides a perspective view depicting a portion of the frame member 412 and the sealing skirt 449; however, for clarity of illustration, the upper skirt 443, the lower skirt 445 and the leaflet assembly 434 are not depicted.

The dimensions of the sealing skirt 449 can be adjusted to obtain the desired amount of material protruding from an expanded annular frame, depending on the type of material used for the sealing skirt. For example, in embodiments where the sealing skirt 449 is constructed of a plush or pile material (such as a loop yarn) having fibers that protrude outwardly between the cells of the frame member 412, the length of the sealing skirt (in an unrolled or flattened configuration prior to mounting on the frame) can be substantially the same as the circumference of the lower portion of the frame member 412. In other embodiments, the length of the sealing skirt prior to mounting on the annular frame is at least about 5% (such as at least about 10%, at least about 15%, at least about 20%, at least about 25%) longer than the circumference of the expanded annular frame of the stent, to allow for additional material to protrude between the cells of the frame member 412.

Although description of the sealing skirt 449 above is made with reference to prosthetic heart valve 410, the sealing skirt can also be included on prosthetic heart valve 10, for example, by modifying the dimensions of the sealing skirt 449 as needed to secure the sealing skirt 449 to skirt assembly 42 of heart valve 10.

The prosthetic valve 410 can be implanted in a retrograde approach where the prosthetic valve, mounted in a crimped state at the distal end of a delivery apparatus (e.g., the delivery apparatus 100), is introduced into the body via the femoral artery and advanced through the aortic arch to the heart, as further described in U.S. Patent Application Publication No. 2008/0065011, which is incorporated herein by reference. The prosthetic valve 410 can also be implanted in a retrograde approach where the prosthetic valve, mounted in a crimped state at the distal end of a delivery apparatus (e.g., the delivery apparatus 100), is introduced into the body via the left or right subclavian artery and advanced to the heart. In further embodiments, the prosthetic valve 410 can be implanted in an antegrade approach where the prosthetic valve, mounted in a crimped state at the distal end of a delivery apparatus, is introduced into the body and advanced transventricularly (see, e.g., U.S. Pat. No. 8,439,970, which is incorporated herein by reference. For transventricular implant applications, the retaining arms 430 can be included on the lower portion of the stent.

Prior to insertion of the delivery apparatus, an introducer sheath can be inserted into the artery followed by a guide wire, which is advanced through the patient's vasculature through the aorta and into the left ventricle. The delivery apparatus can then be inserted through the introducer sheath and advanced over the guide wire until the distal end portion of the delivery apparatus containing the prosthetic valve 410 is advanced to a location adjacent to or within the native aortic valve.

Figures 40A, 40B, 41, 42:
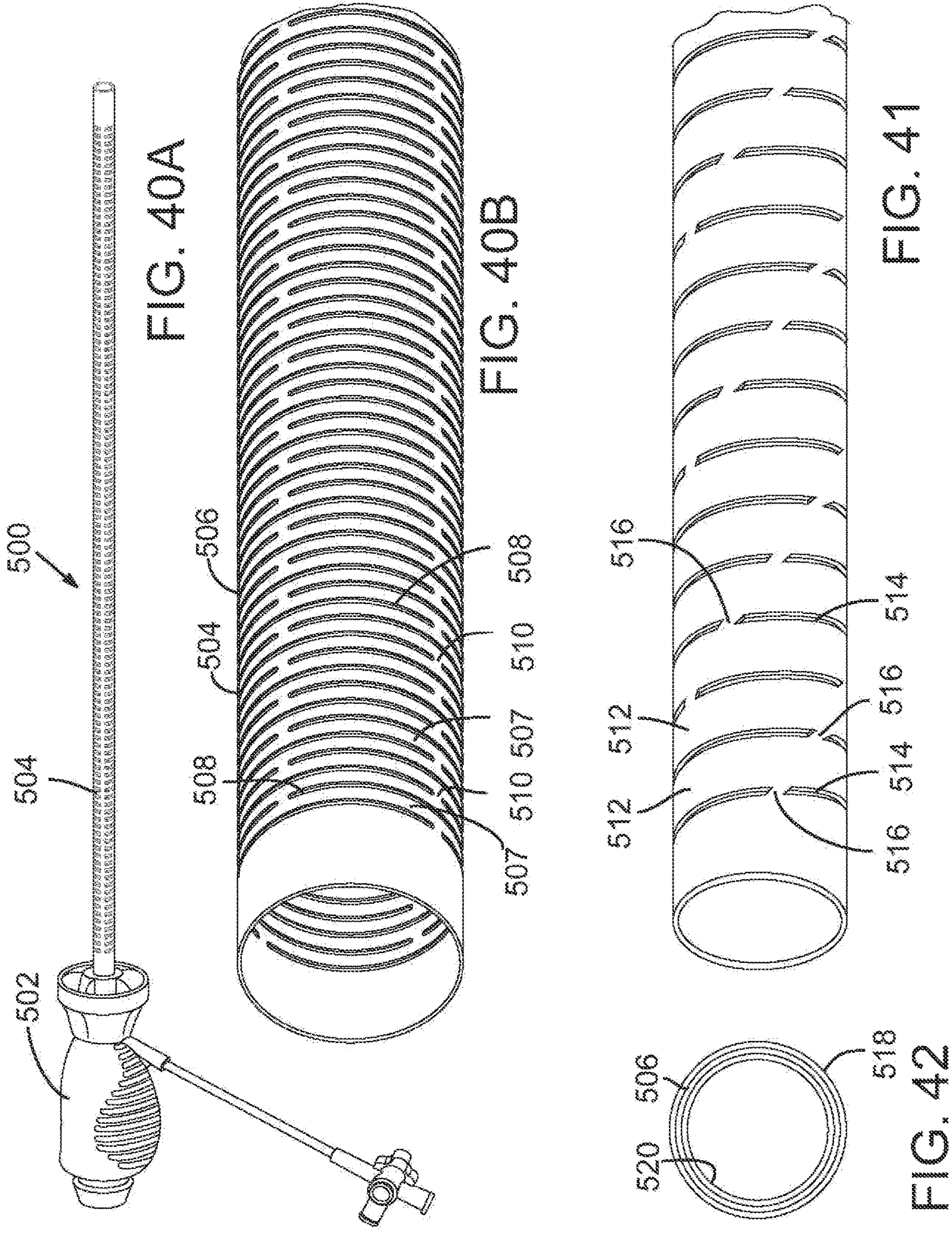
FIG. 40A is a perspective view of an introducer sheath, according to another embodiment.
FIG. 40B is an enlarged, perspective view of the sleeve of the introducer sheath of FIG. 40A.
FIG. 41 is an enlarged, perspective view of another embodiment of a sleeve that can be used with the introducer sheath of FIG. 40A.
FIG. 42 is an end view of a sleeve that can be used with the introducer sheath of FIG. 40A.

Known introducer sheaths typically employ a sleeve made from polymeric tubing having a radial wall thickness of from about 0.025 mm (about 0.010 inch) to about 0.04 mm (about 0.015 inch). FIG. 40A shows an embodiment of an introducer sheath, indicated at 500, that employs a thin metallic tubular layer that has a much smaller wall thickness compared to known devices. In particular embodiments, the wall thickness of the sheath 500 is from about 0.0012 mm (about 0.0005 inch) to about 0.05 mm (about 0.002 inch). The introducer sheath 500 includes a proximally located housing or hub 502 and a distally extending sleeve or cannula 504. The housing 502 can house a seal or a series of seals as known in the art to minimize blood loss. The sleeve 504 comprises a tubular layer or sleeve 506 that is formed from a metal or metal alloy, such as Nitinol or stainless steel, and desirably is formed with a series of circumferentially extending or helically extending slits or openings to impart a desired degree of flexibility to the sleeve.

As shown in FIG. 40B, for example, the tubular layer 506 is formed (e.g., laser cut) with an "I-beam" pattern of alternating circular bands 507 and openings 508 with axially extending connecting portions 510 connecting adjacent bands 507. Two adjacent bands 507 can be connected by a plurality of angularly spaced connecting portions 510, such as four connecting portions 510 spaced about 90 degrees from each other around the axis of the sleeve, as shown in the illustrated embodiment. The sleeve 504 exhibits sufficient flexibility to allow the sleeve to flex as it is pushed through a tortuous pathway without kinking or buckling. FIG. 41 shows another pattern of openings that can be laser cut or otherwise formed in the tubular layer 506. The tubular layer in the embodiment of FIG. 41 has a pattern of alternating bands 512 and openings 514 with connecting portions 516 connecting adjacent bands 512, the openings 514 and connecting portions 516 each arranged in a helical pattern along the length of the sleeve. In alternative embodiments, the pattern of bands and openings and/or the width of the bands and/or openings can vary along the length of the sleeve in order to vary stiffness of the sleeve along its length. For example, the width of the bands can decrease from the proximal end to the distal end of the sleeve to provide greater stiffness near the proximal end and greater flexibility near the distal end of the sleeve.

As shown in FIG. 42, the sleeve 504 can have a thin outer layer or liner 518 extending over the tubular layer 506, the outer layer 518 made of a low friction material to reduce friction between the sleeve and the vessel wall into which the sleeve is inserted. The sleeve 504 can also have a thin inner layer or liner 520 covering the inner surface of the tubular layer 506 and made of a low friction material to reduce friction between the sleeve and the delivery apparatus that is inserted into the sleeve. The inner and outer layers can be made from a suitable polymer, such as PET, PTFE, FEP, and/or polyether block amide (PEBAX®). The inner and outer liners, and the tubular layer, are sized appropriately for the desired application of the introducer sheath 500. In particular embodiments, the inner liner 520 can have a radial wall thickness in the range of from about 0.0012 mm (about 0.0005 inch) to about 0.012 mm (about 0.005 inch) (such as from about 0.025 mm (about 0.001 inch) to about 0.075 mm (0.003 inch), for example about 0.06 mm (about 0.0025 inch)). In particular embodiments, the outer liner 518 has a radial wall thickness in the range of about from about 0.0012 mm (0.0005 inch) to about 0.012 mm (about 0.005 inch) (such as from about 0.012 mm (about 0.0005 inch) to about 0.075 mm (0.003 inch), for example about 0.025 mm (about 0.001 inch)). In particular embodiments, the tubular layer 506 can have a radial wall thickness in the range of from about 0.0012 mm (about 0.0005 inch) to about 0.025 mm (about 0.01 inch) (such as from about 0.05 mm (about 0.002 inch) to about 0.15 mm (about 0.006 inch), for example about 0.05 mm (about 0.002 inch) or about 0.1 mm (about 0.004 inch)).

Together, the inner liner 520, the tubular layer 506, and the outer layer 518, have a wall thickness that can vary based on the desired final product. In some embodiments, the inner liner 520, the tubular layer 506, and the outer layer 518, together can have a radial wall thickness in the range of from about 0.05 mm (about 0.002 inch) to about 0.5 mm (about 0.02 inch) (such as from about 0.09 mm (about 0.0035 inch) to about 0.3 mm (about 0.012 inch). As such, the sleeve 504 can be provided with an outer diameter that is about 1-2 Fr smaller than known devices. The relatively smaller profile of the sleeve 504 improves ease of use, lowers risk of patient injury via tearing of the arterial walls, and increases the potential use of minimally invasive procedures (e.g., heart valve replacement) for patients with highly calcified arteries, tortuous pathways or small vascular diameters.

The inner liner 520 can be applied to the interior of the tubular layer 506, for example, using a two-stage molding process. In one step, a preform, cylindrical polymer tube or parison 522 (FIG. 48) with an open end 524 and a closed end

526 is formed, e.g., by an injection molding or extrusion process. The tube 522 has an outer diameter less than that of the inner diameter of the tubular layer 506, and a wall thickness designed to provide an appropriate thickness for the inner liner 520 of the tubular layer 506, following blow molding. In one embodiment, the tube 522 can have a wall thickness of from about 0.025 mm (about 0.001 inch) to about 0.1 mm (about 0.004 inch) (such as from about 0.05 mm (about 0.002 inch) to about 0.075 mm (about 0.003 inch), such as about 0.06 mm (about 0.0025 inch)). Appropriate material for the polymer tube can be selected based on the desired finished product. In some embodiments, the polymer tube 522 is made of nylon-12, polyethylene, fluorinated ethylene propylene, and/or polyether block amide (, e.g., PEBAX® 72D). The length of the tube 522 can be varied depending on the length of the tubular layer 506, and is typically longer than that of the tubular layer 506. In another step, heat and pressure are applied to the tube 522 to form the inner liner 520 by blow molding.

Figure 48:
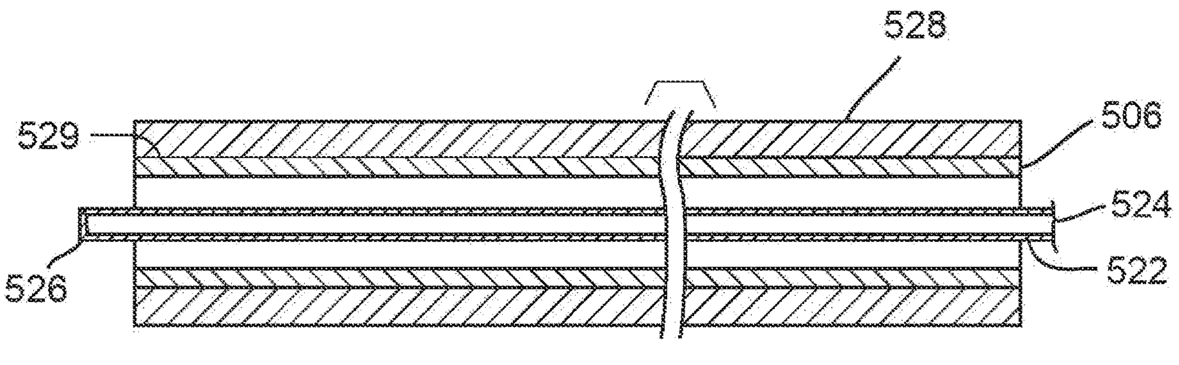
FIGS. 48 and 49 are cross-sectional views illustrating a method of molding an inner liner for a metal sleeve of an introducer sheath.
Figure 49:
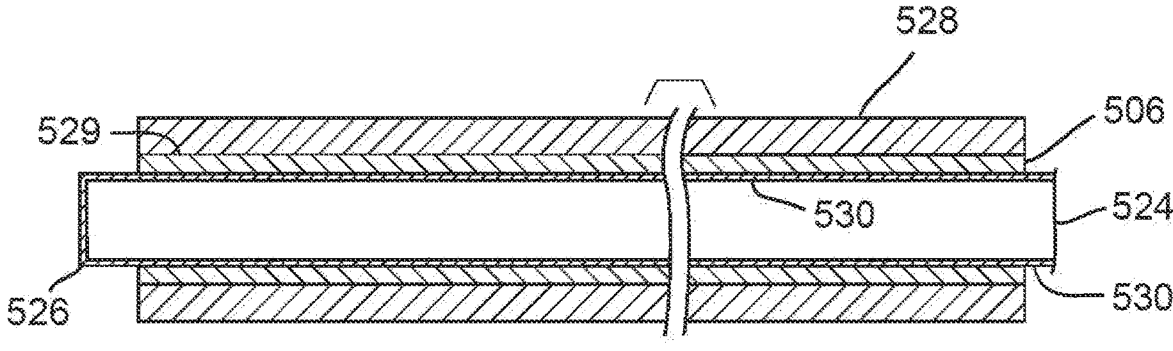

FIGS. 48 and 49 depict an exemplary method of using blow molding to apply the tube 522 to the tubular layer 506 to form the inner liner 520. The tubular layer 506 is inserted into mold 528. The mold 528, which has an inner diameter that is slightly larger than the outer diameter of the tubular layer 506 such that the sleeve can be easily inserted into and removed from the mold, prevents any appreciable radial expansion of the sleeve during the pressurization step (described below). The mold 528 can be constructed to be non-expandable during blow molding of the tube 522. The mold 528 can have a cylindrical inner surface 529 that corresponds to the shape of the outer surface of the tubular layer 506. Thus, when the tube 522 is pressurized (discussed in detail below), the inner surface of the mold prevents the tubular layer 506 from expanding/deforming under pressure from the expanding tube 522 and prevents portions of the tube 522 from expanding radially outwardly through the openings 508 in the tubular layer 506.

The tube 522 with the open end 524 and the closed end 526 is inserted into the tubular layer 506, as shown in FIG. 48. The closed end 526 can extend beyond one end of the tubular layer 506, and the open end 524 can extend beyond the other end of tubular layer 506.

Heat and pressure are applied to the tube 522 to cause the tube to expand against the inner surface of the tubular layer 506 to form an expanded polymer tube 530. The heat and pressure can be applied sequentially (e.g., heat is applied, then pressure), or simultaneously. For example, the heat and pressure can be applied simultaneously by injecting heated compressed gas or liquid into the open end 524 of the tube 522. Alternatively, the heat can be applied by heating the mold 528, and the tube 522 can be pressurized by injecting compressed gas or liquid into the open end 524 of the tube 522. For example, the entire assembly including the mold 528, the tubular layer 506, and the tube 522 can be immersed in a heated fluid. In this regard, the wall of the mold can have one or more apertures that allow the heated fluid (e.g., a heated liquid such as water) to flow through the apertures and contact the tube 522 to facilitate heating of the tube. Various other types of heat sources, such as resistive, conductive, convective, and infrared heat sources, can be used to apply heat to the tube 522. Optionally, the tube 522 can be stretched axially concurrently with heating and/or pressurizing, or in one or more separate stretching steps performed at separate times from heating and/or pressurizing.

Portions of the expanded tube 530 extending beyond the either end of tubular layer 506 can be trimmed to form the inner liner 520 of tubular layer 506. In some embodiments, the inner liner 520 can expand into the openings 508 of the tubular layer 506 during the molding process, and remain in the openings following the molding process. In other embodiments, the inner liner 520 does not expand into and/or remain into the openings 508 of the tubular layer 506 during the molding process. The specific heat and pressure conditions (including the duration for which the heat and pressure should be applied, as well as cooling conditions) for blow molding the inner liner 520 of the tubular layer 506 can be varied as desired, and typically will depend on the starting materials and desired finished product. In some embodiments, the tube 522 is heated to about 125° C. (about 255° F.) and pressurized to about 80 kPa (about 12 psi) for a period of time sufficient to form inner liner 520. Further, general methods of blow molding are known to the person of ordinary skill in the art (see, e.g., U.S. Patent Application Publication No. 2011/0165284, which is incorporated by reference herein in its entirety).

The outer layer 518 of the sheath can be applied over and secured to the outer surface of the tubular layer 506 using conventional techniques or mechanisms (e.g., using an adhesive or by thermal welding). In one embodiment, the outer layer is formed by shrink wrapping a polymer tubular layer to tubular layer 506. Appropriate material for the outer layer 518 can be selected based on the desired finished product. In some embodiments, the outer layer 518 is made of nylon-12, polyether block amide (PEBAX®, e.g., PEBAX® 72D), and/or polyethylene. The outer layer 518 can be applied to the tubular layer 506 before or after the inner layer 520 has been formed using the molding process described above.

In a modification of the introducer sheath 500, the sheath can have inner and outer layers 520, 518, respectively, which are secured to a metal sleeve (e.g., sleeve 504) only at the proximal and distal ends of the metal sleeve. The inner and outer polymeric layers can be bonded to the metal sleeve (or to each other through the gaps in the metal sleeve), for example using a suitable adhesive or by thermal welding. In this manner, the metal sleeve is unattached to the inner and outer polymeric layers between the proximal and distal ends of the sleeve along the majority of the length of the sleeve, and therefore is "free-floating" relative to the polymeric layers along the majority of the length of the sleeve. This construction allows the adjacent bands of metal to bend more easily relative to the inner and outer layers, providing the sheath with greater flexibility and kink-resistance than if the inner and outer layers were bonded along the entire length of the sleeve.

Figures 43, 44, 45, 46, 47:
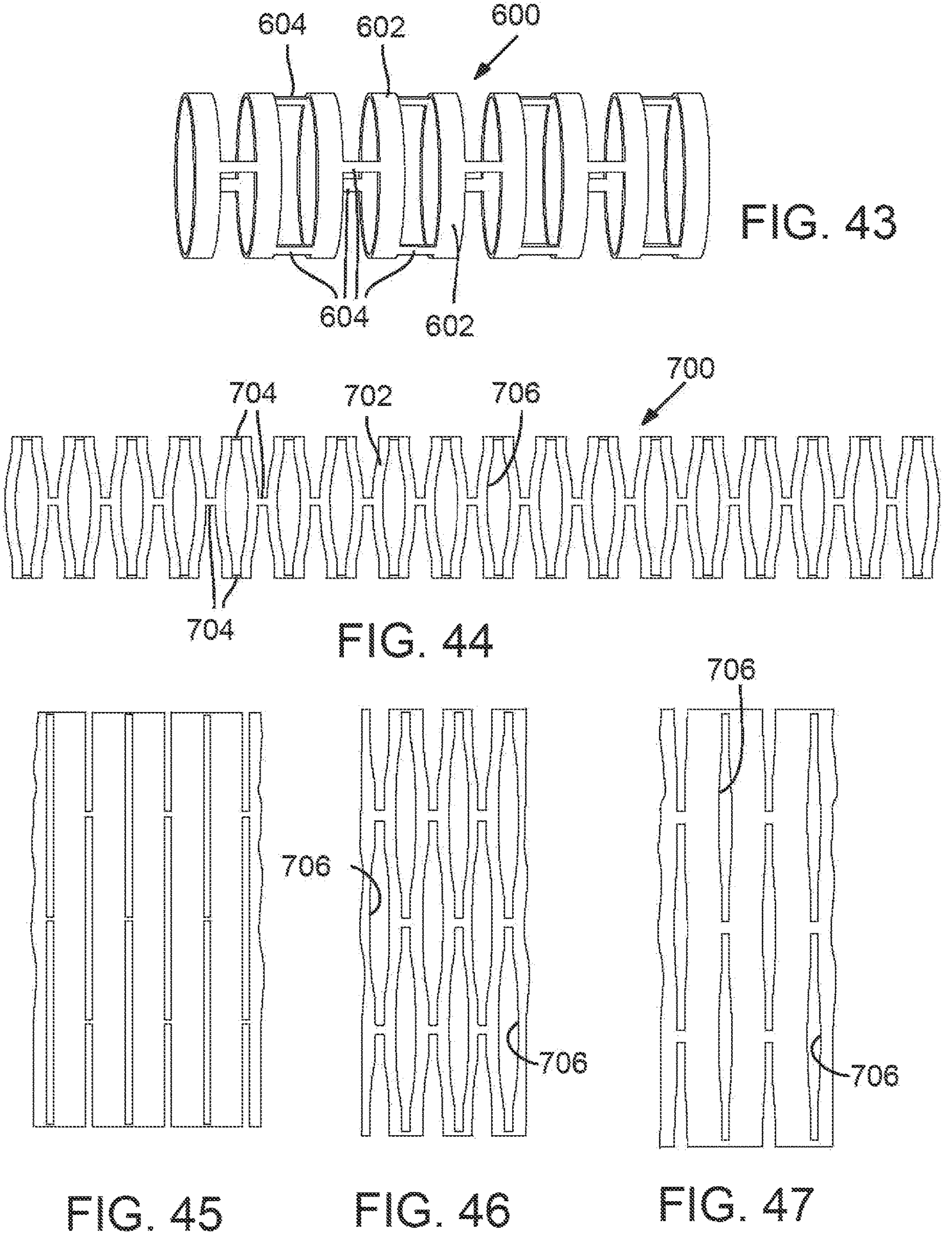
FIG. 43 is a perspective view of a segment of a sleeve of an introducer sheath, according to another embodiment.
FIG. 44 is a side elevation view of a metal sleeve for an introducer sheath, according to another embodiment.
FIG. 45 shows the cut pattern for forming the metal sleeve of FIG. 43.
FIG. 46 shows the cut pattern for forming the metal sleeve of FIG. 44.
FIG. 47 shows a cut pattern similar to FIG. 46 but having narrower apertures.

FIG. 43 shows a segment of an alternative metal sleeve, indicated at 600, that can be used in the introducer sheath 500. The sheath 500 in this embodiment desirably includes inner and outer polymeric layers, which desirably are secured to the metal sleeve only at its proximal and distal ends as discussed above. The sleeve 600 includes a plurality of circular bands or rings 602 interconnected by two links, or connecting portions, 604, extending between each pair of adjacent rings. Each pair of links connecting two adjacent bands 602 desirably are spaced about 180 degrees from each other and desirably are rotationally offset by about 90 degrees from an adjacent pair of links, which allows for multi-axial bending.

FIG. 44 shows side view of a segment of another embodiment of a metal sleeve, indicated at 700, that can be used in the introducer sheath 500. The sleeve 700 has the same cut pattern as the sleeve 600, and therefore has circular bands 702 and two links 704 connecting adjacent bands, and further includes two cutouts, or apertures, 706 formed in each band 702 to increase the flexibility of the sleeve. The cutouts 706 desirably have a generally elliptical or oval shape, but can have other shapes as well. Each cutout 706 desirably extends about 180 degrees in the circumferential direction of the sleeve and desirably is rotational offset by about 90 degrees from a cutout 706 in an adjacent band 702.

In particular embodiments, the metal sleeve of an introducer sheath has a wall thickness in the range of from about 0.05 mm (about 0.002 inch) to about 0.015 mm (about 0.006 inch). In one implementation, a sheath has a metal sleeve having a wall thickness of about 0.05 mm (about 0.002 inch) and an inner diameter of about 5.8 mm (about 0.229 inch), an inner polymeric layer having a wall thickness of about 0.06 mm (about 0.0025 inch), an outer polymeric layer having a wall thickness of about 0.025 mm (about 0.001 inch), and a total wall thickness (through all three layers) of about 0.14 mm (about 0.0055 inch). In another implementation, a sheath has a metal sleeve having a wall thickness of about 0.1 mm (about 0.004 inch) and an inner diameter of about 5.8 mm (about 0.229 inch), an inner polymeric layer having a wall thickness of about 0.06 mm (about 0.0025 inch), an outer polymeric layer having a wall thickness of about 0.025 mm (about 0.001 inch), and a total wall thickness (through all three layers) of about 0.2 mm (about 0.0075 inch). FIG. 45 shows the cut pattern for forming the metal sleeve 600 of FIG. 43. FIG. 46 shows the cut pattern for forming the metal sleeve 700 of FIG. 44. FIG. 47 shows a cut pattern similar to the cut pattern of FIG. 46, but including cutouts 706 that are narrower than the cutouts shown in FIG. 46.

TABLE 1

| Wall thickness of metal sleeve | Material | Minimum bend radius without visual kink | Minimum bend radius allowing passage of 16-Fr dilator |
|---|---|---|---|
| 0.1 mm (0.004") | Nitinol | 2.5 cm (1") | 2.5 cm (1") |
| 0.1 mm (0.004") | Stainless steel | 2.5 cm (1") | 2.5 cm (1") |
| 0.1 mm (0.002") | Nitinol | 15 cm (6") | 2.5 cm (1") |
| 0.05 mm (0.002") | Stainless steel | 15 cm (6") | 2.5 cm (1") |
| 0.05 mm (0.002") | Stainless steel (wide rings) | 5 cm (2") | 2.5 cm (1") |

Table 1 above demonstrates the bend performance of several metal sleeves. Each metal sleeve had an inner diameter of about 5.8 mm (about 0.229 inch). Each sleeve was formed with the cut pattern shown in FIG. 44, except for the last sleeve in Table 1, which was formed with the cut pattern shown in FIG. 43. All of the sleeves in Table 1 provide device deliverability at a relatively small bend radius (2.5 cm, 1 inch). Furthermore, it was found that the metal sleeves recover their circular cross-sectional shapes even after passing a delivery device through a visibly kinked section of the sleeve.

In view of the many possible embodiments to which the principles of the disclosed invention may be applied, it should be recognized that the illustrated embodiments are only preferred examples and should not be taken as limiting the scope of the disclosure. Moreover, additional embodiments are disclosed in U.S. Patent Application Publication No. 2010/0049313 (U.S. patent application Ser. No. 12/429,040) and U.S. Patent Application Publication No. 2012/0239142 (U.S. patent application Ser. No. 13/405,119), each of which is incorporated herein by reference. Accordingly, the scope of the disclosure is defined by the following claims. We therefore claim all that comes within the scope and spirit of these claims.

What is claimed is:

1. A prosthetic heart valve, comprising:

a collapsible and expandable annular frame that is configured to be collapsed to a radially collapsed state for mounting on a delivery apparatus and expanded to a radially expanded state inside a patient's body, the frame having an inflow end, an outflow end, and a longitudinal axis extending from the inflow end to the outflow end, the frame comprising a plurality of rows of angled struts, including a first row of angled struts defining the inflow end of the frame, a second row of angled struts downstream of the first row of angled struts, a third row of angled struts downstream of the second row of angled struts, and a fourth row of angled struts downstream of the third row of angled struts and defining the outflow end of the frame, wherein the first and second rows of angled struts define an inflow row of cells and the third and fourth rows of angled struts define an outflow row of cells;

a leaflet assembly mounted within the frame, wherein the leaflet assembly comprises a plurality of leaflets, wherein each leaflet comprises an inflow end portion and an outflow end portion, wherein adjacent leaflets are connected to each other at the outflow end portions to form commissures of the leaflet assembly, wherein each commissure is aligned with one of the cells of the outflow row of cells and secured to two angled struts of the third row of angled struts and two angled struts of the fourth row of angled struts with sutures, wherein the sutures form multiple stitches that extend around and are spaced along a length of each of the two angled struts of the third row and each of the two angled struts of the fourth row at each commissure;

a first skirt mounted on the frame, wherein the first skirt has an inflow end portion and an outflow end portion, wherein the inflow end portions of the leaflets are sutured to the outflow end portion of the first skirt along an undulating suture line, wherein the outflow end portion of the first skirt has an undulating shape that corresponds with the undulating suture line; and a second skirt mounted on the frame radially outward from the first skirt, wherein the second skirt has an inflow end portion and an outflow end portion.

2. The prosthetic heart valve of claim 1, wherein the second skirt comprises a pile fabric.

3. The prosthetic heart valve of claim 2, wherein the pile fabric is made of loop yarn.

4. The prosthetic heart valve of claim 3, wherein the loop yarn comprises polyethylene terephthalate loop yarn.

5. The prosthetic heart valve of claim 2, wherein the pile fabric is made of textured yarn.

6. The prosthetic heart valve of claim 1, wherein the inflow row of cells defines a plurality of apices at the inflow end of the frame and the inflow end portion of the second skirt extends beyond the apices when the frame is in the radially expanded state.

7. The prosthetic heart valve of claim 1, wherein the outflow end portion of the second skirt comprises a straight upper edge that transects the cells of one of the rows of cells.

8. The prosthetic heart valve of claim 1, wherein the frame comprises exactly four rows of cells.

9. The prosthetic heart valve of claim 1, wherein the cells are diamond shaped.

10. The prosthetic heart valve of claim 1, wherein the first skirt comprises a woven fabric and the second skirt comprises a knitted fabric.

11. A method of implanting the prosthetic heart valve of claim 1, wherein the method comprises:

inserting an introducer sheath into a blood vessel of a patient, wherein the introducer sheath comprises a tubular layer, an inner liner covering an inner surface of the tubular layer, and an outer layer covering an outer surface of the tubular layer, wherein the tubular layer comprises a metal or metal alloy;

inserting a distal end portion of the delivery apparatus through the introducer sheath and into the blood vessel, wherein the prosthetic heart valve is in a radially compressed state on the distal end portion of the delivery apparatus;

deploying the prosthetic heart valve in a native annulus of the heart.

12. A prosthetic heart valve, comprising:

a collapsible and expandable annular frame that is configured to be collapsed to a radially collapsed state for mounting on a delivery apparatus and expanded to a radially expanded state inside a patient's body, the frame having an inflow end, an outflow end, and a longitudinal axis extending from the inflow end to the outflow end, the frame comprising a plurality of struts, including a first row of angled struts defining the inflow end of the frame, a second row of angled struts downstream of the first row of angled struts, a third row of angled struts downstream of the second row of angled struts, a fourth row of angled struts downstream of the third row of angled struts, and a fifth row of angled struts downstream of the fourth row of angled struts and defining the outflow end of the frame, wherein the first and second rows of angled struts define a first, inflow row of cells, the second and third row of angled struts define a second row of cells downstream of the first row of cells, the third and fourth row of angled struts define a third row of cells downstream of the second row of cells, and the fourth and fifth row of angled struts define a fourth, outflow row of cells;

a leaflet assembly mounted within the frame, wherein the leaflet assembly comprises a plurality of leaflets, wherein each leaflet comprises an inflow end portion and an outflow end portion, wherein adjacent leaflets are connected to each other at the outflow end portions to form commissures of the leaflet assembly, wherein each commissure is aligned with one of the cells of the fourth row of cells and secured to two angled struts of the fourth row of angled struts and two angled struts of the fifth row of angled struts with sutures, wherein the sutures form multiple stitches that extend around and are spaced along a length of each of the two angled struts of the fourth row and each of the two angled struts of the fifth row at each commissure;

a first skirt mounted on the frame, wherein the first skirt has an inflow end portion and an outflow end portion, wherein the inflow end portions of the leaflets are sutured to the outflow end portion of the first skirt along an undulating suture line, wherein the outflow end portion of the first skirt has an undulating shape that corresponds with the undulating suture line, wherein the first skirt covers cells of the first and second rows of cells; and a second skirt mounted on the frame radially outward from the first skirt, wherein the second skirt has an inflow end portion and an outflow end portion;

wherein the first skirt extends from the inflow end of the frame and overlaps the second skirt along an inflow end portion of the frame and extends beyond the outflow end portion of the second skirt in a direction toward the outflow end of the frame.

13. The prosthetic heart valve of claim 12, wherein the frame comprises exactly four rows of cells.

14. The prosthetic heart valve of claim 12, wherein the cells are diamond shaped.

15. The prosthetic heart valve of claim 12, wherein the first skirt comprises a woven fabric and the second skirt comprises a knitted fabric.

16. The prosthetic heart valve of claim 12, wherein the outflow end portion of the second skirt comprises a straight upper edge.

17. The prosthetic heart valve of claim 16, wherein the inflow end portion of the second skirt comprises a straight lower edge.

18. The prosthetic heart valve of claim 12, wherein the suture line transects struts that form the first row of cells.

19. The prosthetic heart valve of claim 12, wherein the second skirt comprises a pile fabric.

20. The prosthetic heart valve of claim 19, wherein the pile fabric is made of textured yarn.

21. The prosthetic heart valve of claim 12, wherein the cells of the fourth row of cells have the same size and shape.

* * * * *